(12) United States Patent
Tallent et al.

(10) Patent No.: US 12,042,451 B2
(45) Date of Patent: Jul. 23, 2024

(54) CABLE-FREE BED WITH WIRELESS PILLOW SPEAKER

(71) Applicant: Hill-Rom Services, Inc., Batesville, IN (US)

(72) Inventors: Dan R. Tallent, Hope, IN (US);
Richard J. Schuman, Cary, NC (US);
Eric D. Benz, Sunman, IN (US);
Unnati Ojha, Apex, NC (US);
Frederick Collin Davidson, Apex, NC (US); Darren S. Hudgins, Cary, NC (US); Jason M. Williams, Cary, NC (US)

(73) Assignee: Hill-Rom Services, Inc., Batesville, IN (US)

( * ) Notice: Subject to any disclaimer, the term of this patent is extended or adjusted under 35 U.S.C. 154(b) by 459 days.

(21) Appl. No.: 17/383,488

(22) Filed: Jul. 23, 2021

(65) Prior Publication Data
US 2022/0054337 A1     Feb. 24, 2022

Related U.S. Application Data

(60) Provisional application No. 63/068,561, filed on Aug. 21, 2020.

(51) Int. Cl.
*A61G 7/05* (2006.01)
*H04W 76/11* (2018.01)
*H04W 76/14* (2018.01)

(52) U.S. Cl.
CPC .......... *A61G 7/0524* (2016.11); *H04W 76/11* (2018.02); *H04W 76/14* (2018.02)

(58) Field of Classification Search
CPC ...... G16H 50/20; H04W 76/14; H04W 76/11; H04W 76/02; H04W 4/02; H04L 61/1535; H04B 5/00
See application file for complete search history.

(56) References Cited

U.S. PATENT DOCUMENTS

| 4,183,015 A | 1/1980 | Drew et al. |
| 5,561,412 A | 10/1996 | Novak et al. |

(Continued)

FOREIGN PATENT DOCUMENTS

| CN | 108370502 A | 8/2018 |
| CN | 209447286 | 9/2019 |

(Continued)

OTHER PUBLICATIONS

COMLinx® Nurse Communication Module User Manual P000434 rev. 4 Version 3.4; © 2005; 395 pages.

(Continued)

*Primary Examiner* — Iqbal Zaidi
(74) *Attorney, Agent, or Firm* — Barnes & Thornburg LLP

(57) ABSTRACT

A system and method of patient bed communication and bed-to-room association in a healthcare facility having a network with at least one wireless access point (WAP) and a nurse call system is provided. A handheld unit is moved to a position within a pairing distance of a pairing zone of a patient bed so that the handheld unit and the bed are paired using a first wireless communication technology. A second wireless communication technology is used to send bed identification data (ID) to the handheld unit after the pairing operation has been completed. The bed ID is transmitted from the handheld unit to the nurse call system via a wired connection to establish a bed-to-room association between the patient bed and a room in which the patient bed is located. A third wireless communication technology is used to send bed status data and the bed ID to the WAP of the network.

20 Claims, 10 Drawing Sheets

(56) References Cited

U.S. PATENT DOCUMENTS

| | | |
|---|---|---|
| 5,699,038 A | 12/1997 | Ulrich et al. |
| 5,838,223 A | 11/1998 | Gallant et al. |
| 6,005,486 A | 12/1999 | Fridley et al. |
| 6,008,736 A | 12/1999 | Palm et al. |
| 6,147,592 A | 11/2000 | Ulrich et al. |
| 6,362,725 B1 | 3/2002 | Ulrich et al. |
| 6,366,328 B1 | 4/2002 | Vanderpohl, III et al. |
| 6,759,607 B2 | 7/2004 | Engler |
| 6,897,780 B2 | 5/2005 | Ulrich et al. |
| 6,958,706 B2 | 10/2005 | Chaco et al. |
| 7,092,376 B2 | 8/2006 | Schuman |
| 7,242,308 B2 | 7/2007 | Ulrich et al. |
| 7,315,535 B2 | 1/2008 | Schuman |
| 7,319,386 B2 | 1/2008 | Collins, Jr. et al. |
| 7,538,659 B2 | 5/2009 | Ulrich et al. |
| 7,715,387 B2 | 5/2010 | Schuman |
| 7,746,218 B2 | 6/2010 | Collins, Jr. et al. |
| 7,831,447 B2 | 11/2010 | Schuman |
| 7,868,740 B2 | 1/2011 | McNeely et al. |
| 8,031,057 B2 | 10/2011 | McNeely et al. |
| 8,046,625 B2 | 10/2011 | Ferguson et al. |
| 8,125,318 B2 | 2/2012 | Heimbrock et al. |
| 8,143,846 B2 | 3/2012 | Herman et al. |
| 8,169,304 B2 | 5/2012 | Schuman, Sr. et al. |
| 8,254,137 B2 | 8/2012 | Wilkolaski et al. |
| 8,384,526 B2 | 2/2013 | Schuman, Sr. et al. |
| 8,392,747 B2 | 3/2013 | Ferguson et al. |
| 8,456,286 B2 | 6/2013 | Schuman et al. |
| 8,598,995 B2 | 12/2013 | Schuman et al. |
| 8,604,916 B2 | 12/2013 | McNeely et al. |
| 8,762,766 B2 | 6/2014 | Ferguson et al. |
| 8,779,924 B2 | 7/2014 | Pesot et al. |
| 8,803,668 B2 | 8/2014 | Schuman et al. |
| 8,803,669 B2 | 8/2014 | Schuman, Sr. et al. |
| 9,235,979 B2 | 1/2016 | Schuman, Sr. et al. |
| 9,299,242 B2 | 3/2016 | Schuman et al. |
| 9,375,374 B2 | 6/2016 | Herman et al. |
| 9,411,934 B2 | 8/2016 | Robinson et al. |
| 9,465,915 B2 | 10/2016 | McNeely et al. |
| 9,466,877 B2 | 10/2016 | Dixon et al. |
| 9,517,035 B2 | 12/2016 | Schuman et al. |
| 9,734,293 B2 | 8/2017 | Collins, Jr. et al. |
| 9,830,424 B2 | 11/2017 | Dixon et al. |
| 9,955,926 B2 | 5/2018 | Schuman et al. |
| 10,123,925 B2 | 11/2018 | Herman et al. |
| 10,163,322 B2 | 12/2018 | Ribble et al. |
| 10,176,700 B2 | 1/2019 | Dixon et al. |
| 10,290,071 B2 | 5/2019 | Heil et al. |
| 10,307,113 B2 | 6/2019 | Schuman et al. |
| 10,339,789 B1 | 7/2019 | MacDonald |
| 10,360,787 B2 | 7/2019 | Embree et al. |
| 10,561,549 B2 | 2/2020 | Walton et al. |
| 10,601,971 B2 | 3/2020 | Hatch et al. |
| 10,638,983 B2 | 5/2020 | Schuman et al. |
| 10,910,102 B2 | 2/2021 | Agdeppa et al. |
| 10,916,119 B2 | 2/2021 | Baker et al. |
| 10,958,311 B2 | 3/2021 | Ayers et al. |
| 10,979,046 B2 | 4/2021 | MacDonald |
| 11,011,267 B2 | 5/2021 | Dixon et al. |
| 11,013,418 B2 | 5/2021 | Ayers et al. |
| 11,058,368 B2 | 7/2021 | Schuman et al. |
| 11,062,707 B2 | 7/2021 | Judy et al. |
| 2006/0056616 A1 | 3/2006 | Heimbrock |
| 2009/0212925 A1 | 8/2009 | Schuman, Sr. et al. |
| 2009/0212956 A1 | 8/2009 | Schuman et al. |
| 2009/0214009 A1 | 8/2009 | Schuman, Sr. et al. |
| 2009/0217080 A1 | 8/2009 | Ferguson et al. |
| 2013/0069771 A1* | 3/2013 | Frondorf .............. A61B 5/0002 340/286.07 |
| 2015/0081335 A1 | 3/2015 | Dixon et al. |
| 2015/0257952 A1* | 9/2015 | Zerhusen ............... A61G 7/053 340/12.5 |
| 2016/0065268 A1 | 3/2016 | Dobyns et al. |
| 2018/0161225 A1 | 6/2018 | Zerhusen et al. |
| 2019/0108908 A1 | 4/2019 | Faulks et al. |
| 2019/0183705 A1 | 6/2019 | Bodurka |
| 2019/0188992 A1 | 6/2019 | Bodurka et al. |
| 2019/0336085 A1 | 11/2019 | Kayser et al. |
| 2019/0374039 A1 | 12/2019 | Hosokawa et al. |
| 2020/0066415 A1 | 2/2020 | Hettig et al. |
| 2020/0365364 A1 | 11/2020 | Shintani et al. |
| 2021/0267555 A1* | 9/2021 | Janssen .................. A61B 5/002 |

FOREIGN PATENT DOCUMENTS

| | | |
|---|---|---|
| DE | 102013206841 | 5/2018 |
| EP | 2860651 A1 | 4/2015 |
| FR | 3016517 | 7/2015 |

OTHER PUBLICATIONS

The COMposer® System Installation Manual; © 2003; 225 pages.

COMLinx® Nurse Communication Module Data Sheets P001052 rev. 3; © 2005; 108 pages.

First Office Action issued in Chinese Patent Application No. 202110915125.7 on Oct. 28, 2023, and its English translation (18 pages).

Extended European Search Report for European Patent Application No. 21191331.4 dated Feb. 1, 2022 (9 pages).

Second Office Action issued for Chinese Patent Application No. 202110915125.7 on Mar. 9, 2024, and its English translation (17 pages).

* cited by examiner

CABLE-FREE BED WITH WIRELESS PILLOW SPEAKER

The present application claims the benefit, under 35 U.S.C. § 119(e), of U.S. Provisional Patent Application No. 63/068,561, filed Aug. 21, 2020, which is hereby incorporated by reference herein in its entirety.

BACKGROUND

The present disclosure relates to patient beds configured for wireless communication of bed status data and alerts. More particularly, the present disclosure relates to communication between patient beds and nurse call systems and also to bed-to-room association systems and methods.

Known patient beds are configured to couple to nurse call systems via wired connections such as nurse call cables. For example, patient beds marketed by Hill-Rom Company, Inc. oftentimes connect to wall-mounted audio station bed connectors (ASBC's) or bed interface units (BIU's) of nurse call systems, such as the NAVICARE® Nurse Call System, using a nurse call cable having male and female 37-pin connectors at its opposite ends. If a caregiver forgets to disconnect the nurse call cable from the ASBC, BIU, or other similar type of wall module prior to attempting to move the patient bed to another location, the nurse call cable can potentially become damaged when it is abruptly ripped out of the wall module. The connector on the wall module or the wall module itself can also potentially become damaged.

In more recent times, patient beds with wireless communication capability have entered the market. However, elimination of the wired connection to a wall module introduces challenges with regard to making bed-to-room associations. For the prior art beds that connect to wall modules using cables, bed identification data (ID) is typically sent to the wall module which contains a location ID or some other ID (e.g., wall module ID, MAC address, or the like) that correlates to the room location. The wall module transmits the bed ID received over the nurse call cable from the bed along with the location ID stored in the wall module to a nurse call system server or some other locating server which is able to determine the bed location based on the received bed and location ID's.

When beds transmit the corresponding bed ID's wirelessly, especially when transmitting using radio frequency (RF) signals, the bed ID's are oftentimes received at multiple wall modules or other fixed receiving units such as wireless access points (WAP's), depending upon the signal strength of the RF transmissions and the wireless technology used for making the RF transmissions. In fact, the RF transmissions from the beds are able to pass through walls, ceilings, and floors in some instances and then are received by wall modules or receiving units in entirely different rooms. Thus, there is a continuing need for improvements in making bed-to-room associations in systems in which patient beds communicate wirelessly with nurse call systems or other portions of a network of a healthcare facility.

SUMMARY

An apparatus, system, or method may comprise one or more of the features recited in the appended claims and/or the following features which, alone or in any combination, may comprise patentable subject matter:

According to a first aspect of the present disclosure, a system of patient bed communication and bed-to-room association in a healthcare facility that may have a network with at least one wireless access point (WAP) and a nurse call system is provided. The system of the first aspect may include a patient bed that may have a frame and circuitry that may be carried by the frame. The circuitry may include a first portion that may be configured for wireless communication according to a first wireless communication technology, a second portion that may be configured for wireless communication according to a second wireless communication technology, and a third portion that may be configured for wireless communication according to a third wireless communication technology. The system of the first aspect may also include a handheld unit that may have a wired connection to the nurse call system.

The handheld unit of the first aspect may have wireless bed interface circuitry that may be in communication with the patient bed according to the first and second wireless communication technologies but not the third wireless communication technology. The first wireless communication technology may be used to perform a pairing operation between the patient bed and the handheld unit when the handheld unit may be manually placed within a pairing distance of four centimeters or less of a pairing zone of the patient bed. The second wireless communication technology may be used to send bed identification data (ID) to the handheld unit after the pairing operation has been completed and with the handheld unit being at a communication distance greater than the pairing distance from the pairing zone. The handheld unit may be configured to transmit the bed ID to the nurse call system to establish a bed-to-room association between the patient bed and a room in which the patient bed may be located. The third wireless communication technology may be used to send bed status data and the bed ID to the WAP of the network.

In some embodiments, the first wireless communication technology of the first aspect may include near field communication (NFC) technology. Optionally, the frame of the patient bed may include a siderail that may be movable between a raised position to block a patient from egressing from the patient bed and a lowered position to permit the patient to egress from the patient bed. The pairing zone may be provided on the siderail. If desired, indicia may be provided on the siderail to visually indicate where the pairing zone may be located on the siderail.

It is contemplated by the present disclosure that the second wireless communication technology of the first aspect may comprise Bluetooth technology. For example, the Bluetooth technology may include Bluetooth Low Energy (BLE) technology. Optionally, the Bluetooth technology may be used to send audio signals between the patient bed and the handheld unit of the first aspect. The present disclosure also contemplates that the third wireless communication technology of the first aspect may comprise WiFi technology according to an 802.11 communication protocol.

In some embodiments of the first aspect, the wired connection to the nurse call system may include a cable that may have a first connector that may couple to a second connector of a wall module of the nurse call system. The wall module of the first aspect may send a location ID along with the bed ID for receipt by a nurse call server of the nurse call system. The location ID may correspond to the room in which the patient bed may be located and may be used to establish the bed-to-room association. If desired, the handheld unit of the first aspect may include a pillow speaker that may include user inputs for (i) sending a nurse call signal to the nurse call system, (ii) controlling room lighting, and (iii) controlling at least one room entertainment device.

It is contemplated by the present disclosure that the circuitry of the patient bed of the first aspect may include a processor and a memory. The memory may store instructions that may be executed by the processor to control or monitor features of the patient bed. For example, the features of the patient bed of the first aspect may include one or more of the following: moving a first portion of the frame relative to a second portion of the frame, inflating or deflating a bladder of a mattress supported by the frame, detecting a position of a siderail coupled to the frame, detecting a caster brake status of one or more casters of the frame, detecting an angle of a head section of the frame relative to horizontal or relative to another portion of the frame, detecting whether a bed exit system of the patient bed may be armed, detecting a patient weight using a weigh scale of the frame, or detecting whether an upper frame portion of the frame may be in its lowest position relative to a base frame portion of the frame. Furthermore, the bed status data sent to the WAP of the network of the first aspect may include information regarding the features of the patient bed.

In some embodiments of the first aspect, the instructions stored in memory also may be executed by the processor to determine alert conditions associated with the patient bed. For example, the alert conditions may include one or more of the following: a head section of the frame being lowered below a threshold angle relative to horizontal or relative to another portion of the frame, a siderail coupled to the frame being lowered, a patient exiting the patient bed, a patient moving to an unwanted position on the patient bed, an inability of a bladder of a mattress supported by the frame to be inflated to a target pressure, one or more casters of the frame becoming unbraked, an upper frame portion of the frame being moved out of its lowest position relative to a base frame portion of the frame, or a patient becoming incontinent on the patient bed. Furthermore, the bed status data sent to the WAP of the network may include information regarding the alert conditions.

If desired, the system of first aspect further may include a wall mount to which the handheld unit may be detachably coupleable. Thus, the wired connection may include a cable of sufficient length to permit the handheld unit to be moved to the pairing zone of the patient bed when the handheld unit is detached from the wall mount. Optionally, the handheld unit of the first aspect may be devoid of any manual user inputs. Alternatively or additionally, the handheld unit of the first aspect may include indicia that may provide instructions regarding the pairing operation.

According to a second aspect of the present disclosure, a system of patient bed communication and bed-to-room association in a healthcare facility having a network with at least one wireless access point (WAP) and a nurse call system may be provided. The system of the second aspect may include a patient bed that may have a frame and circuitry carried by the frame. The circuitry may include a first portion that may be configured for wireless communication according to a first wireless communication technology and a second portion that may be configured for wireless communication according to a second wireless communication technology. The circuitry further may include a graphical user interface (GUI). The system of the second aspect may also include a handheld pillow speaker that may have a wired connection to the nurse call system. The handheld pillow speaker may have wireless bed interface circuitry that may be configured for communication with the patient bed according to the first wireless communication technology but not the second wireless communication technology.

After the handheld pillow speaker of the second aspect establishes wireless communication with the first portion of the circuitry according to the first wireless communication technology, the GUI may display pillow speaker identification data (ID) which may be selectable to initiate a pairing operation between the patient bed and the handheld pillow speaker. The first wireless communication technology may be used by the patient bed of the second aspect to send a bed ID to the handheld pillow speaker after the pairing operation has been completed. The handheld pillow speaker of the second aspect may be configured to transmit the bed ID to the nurse call system to establish a bed-to-room association between the patient bed and a room in which the patient bed is located. The second wireless communication technology of the second aspect may be used to send bed status data and the bed ID to the WAP of the network.

In some embodiments, the first wireless communication technology of the second aspect may comprise Bluetooth technology. For example, the Bluetooth technology may include Bluetooth Low Energy (BLE) technology. Optionally, the Bluetooth technology may be used to send audio signals between the patient bed and the handheld pillow speaker. The present disclosure also contemplates that the second wireless communication technology of the second aspect may comprise WiFi technology according to an 802.11 communication protocol.

The present disclosure contemplates that the wired connection to the nurse call system of the second aspect may include a cable that may have a first connector that may couple to a second connector of a wall module of the nurse call system. The wall module of the second aspect may send a location ID along with the bed ID for receipt by a nurse call server of the nurse call system. The location ID may correspond to the room in which the patient bed is located and may be used to establish the bed-to-room association. If desired, the handheld pillow speaker of the second aspect may include user inputs for (i) sending a nurse call signal to the nurse call system, (ii) controlling room lighting, and (iii) controlling at least one room entertainment device.

It is further contemplated by the present disclosure that the circuitry of the patient bed of the second aspect may include a processor and a memory. The memory may store instructions that are executed by the processor to control or monitor features of the patient bed. For example, the features of the patient bed of the second aspect may include one or more of the following: moving a first portion of the frame relative to a second portion of the frame, inflating or deflating a bladder of a mattress supported by the frame, detecting a position of a siderail coupled to the frame, detecting a caster brake status of one or more casters of the frame, detecting an angle of a head section of the frame relative to horizontal or relative to another portion of the frame, detecting whether a bed exit system of the patient bed may be armed, detecting a patient weight using a weigh scale of the frame, or detecting whether an upper frame portion of the frame may be in its lowest position relative to a base frame portion of the frame. Furthermore, the bed status data sent to the WAP of the network of the second aspect may include information regarding the features of the patient bed.

In some embodiments of the second aspect, the instructions stored in memory also may be executed by the processor to determine alert conditions associated with the patient bed. For example, the alert conditions may include one or more of the following: a head section of the frame being lowered below a threshold angle relative to horizontal or relative to another portion of the frame, a siderail coupled to the frame being lowered, a patient exiting the patient bed, a patient moving to an unwanted position on the patient bed, an inability of a bladder of a mattress supported by the frame to be inflated to a target pressure, one or more casters of the frame becoming unbraked, an upper frame portion of the frame being moved out of its lowest position relative to a base frame portion of the frame, or a patient becoming incontinent on the patient bed. Furthermore, the bed status data sent to the WAP of the network of the second aspect may include information regarding the alert conditions.

Optionally, if the alert condition of the second aspect comprises a patient exiting the patient bed or a patient moving to an unwanted position on the patient bed, the alert condition also may be communicated to the handheld pillow speaker according to the first wireless communication technology. Further optionally, the patient bed of the second aspect may include a siderail that may be coupled to the frame and that may be movable between a raised position to block a patient from egressing from the patient bed and a lowered position to permit the patient to egress from the patient bed. The GUI may be pivotably coupled to the siderail of the second aspect.

If desired, the patient bed of the second aspect may include a nurse call input that may be selectable by a patient to send a nurse call signal. The nurse call signal may be communicated to the handheld pillow speaker from the patient bed using the first wireless communication technology and the handheld pillow speaker may forward the nurse call signal to the nurse call system via the wired connection. Alternatively or additionally, the handheld pillow speaker may include a second nurse call input that also may be selectable by the patient to send the nurse call signal to the nurse call system. The patient bed of the second aspect may include a siderail that may be coupled to the frame and movable between a raised position to block a patient from egressing from the patient bed and a lowered position to permit the patient to egress from the patient bed, and the nurse call input may be coupled to the siderail. In some embodiments, the handheld pillow speaker of the second aspect may be configured to change a format of the nurse call signal prior to forwarding the nurse call signal to the nurse call system.

According to a third aspect of the present disclosure, a method of patient bed communication and bed-to-room association in a healthcare facility having a network with at least one wireless access point (WAP) and a nurse call system may be provided. The method of the third aspect may include manually moving a handheld unit to a position within a pairing distance of four centimeters or less of a pairing zone of a patient bed, pairing the handheld unit and the bed using a first wireless communication technology, using a second wireless communication technology to send bed identification data (ID) to the handheld unit after the pairing operation has been completed and with the handheld unit being at a communication distance greater than the pairing distance from the pairing zone, transmitting the bed ID from the handheld unit to the nurse call system via a wired connection to establish a bed-to-room association between the patient bed and a room in which the patient bed is located, and using a third wireless communication technology to send bed status data and the bed ID to the WAP of the network.

In some embodiments of the method of the third aspect, pairing the handheld unit and the bed using the first wireless communication technology may include using near field communication (NFC) technology. In this regard, using NFC technology may include operating an NFC reader of the patient bed to read a handheld unit ID encoded on an NFC transponder attached to the handheld unit. The method of the third aspect may further include using the second wireless communication technology to send the handheld unit ID back to the handheld unit along with the bed ID.

Optionally, the patient bed of the third aspect may include a frame and a siderail that may be coupled to the frame and movable between a raised position to block a patient from egressing from the patient bed and a lowered position to permit the patient to egress from the patient bed. The pairing zone may be provided on the siderail of the third aspect. If desired, indicia on the siderail of the third aspect may be used to visually indicate where the pairing zone may be located on the siderail.

The present disclosure contemplates that using the second wireless communication technology of the third aspect may include using Bluetooth technology. For example, using Bluetooth technology may include using Bluetooth Low Energy (BLE) technology. Optionally, the method of the third aspect may further include communicating audio signals between the patient bed and the handheld unit using the Bluetooth technology. The present disclosure also contemplates that using the third wireless communication technology of the third aspect may include using WiFi technology according to an 802.11 communication protocol.

In some embodiments of the method of the third aspect, transmitting the bed ID from the handheld unit to the nurse call system via the wired connection may include transmitting the bed ID over a cable that may have a first connector that may couple to a second connector of a wall module of the nurse call system. The method of the third aspect further may include sending a location ID along with the bed ID from the wall module for receipt by a nurse call server of the nurse call system. The location ID data may correspond to the room in which the patient bed may be located and may be used to establish the bed-to-room association. For example, the bed-to-room association may be established by the nurse call server or by another server that may be communicatively coupled to the nurse call server. If desired, the handheld unit of the third aspect may include a pillow speaker that may include user inputs for (i) sending a nurse call signal to the nurse call system, (ii) controlling room lighting, and (iii) controlling at least one room entertainment device.

Optionally, the bed status data sent to the WAP of the network of the third aspect may include information regarding one or more of the following features of the patient bed: a frame position of a first portion of a frame of the patient bed relative to a second portion of the frame, inflation or deflation state of a bladder of a mattress supported by the frame, a siderail position of a siderail coupled to the frame, a caster brake status of one or more casters of the frame, an angle of a head section of the frame relative to horizontal or relative to another portion of the frame, whether a bed exit system of the patient bed may be armed, a patient weight detected using a weigh scale of the frame, or whether an upper frame portion of the frame may be in its lowest position relative to a base frame portion of the frame.

Further optionally, the bed status data sent to the WAP of the network of the third aspect may include information regarding one or more of the following alert conditions of the patient bed: a head section of a frame of the patient bed being lowered below a threshold angle relative to horizontal or relative to another portion of the frame, a siderail coupled to the frame being lowered, a patient exiting the patient bed, a patient moving to an unwanted position on the patient bed, an inability of a bladder of a mattress supported by the frame to be inflated to a target pressure, one or more casters of the frame becoming unbraked, an upper frame portion of the frame being moved out of its lowest position relative to a base frame portion of the frame, or a patient becoming incontinent on the patient bed.

In some embodiments, the method of the third aspect further may include detaching the handheld unit from a wall mount prior to manually moving the handheld unit to the position within the pairing distance of the pairing zone and reattaching the handheld unit to the wall mount after pairing the handheld unit and the bed. Thus, the wired connection of the third aspect may include a cable of sufficient length to permit the handheld unit to be moved to the pairing zone of the patient bed when the handheld unit is detached from the wall mount. If desired, the handheld unit of the third aspect may be devoid of any manual user inputs. Alternatively or additionally, the handheld unit may include indicia that may provide instructions regarding how to pair the handheld unit and the patient bed.

According to a fourth aspect of the present disclosure, a method of patient bed communication and bed-to-room association in a healthcare facility having a network with at least one wireless access point (WAP) and a nurse call system may be provided. The method of the fourth aspect may include providing a patient bed that may have circuitry configured for communication according to a first wireless communication technology and a second wireless communication technology. The patient bed of the fourth aspect also may have a graphical user interface coupled to the circuitry. The method of the fourth aspect may also include receiving a wireless communication from a handheld pillow speaker at the circuitry of a patient bed according to the first communication technology, displaying on the GUI of the patient bed pillow speaker identification data (ID) included in the wireless communication from the handheld pillow speaker, and initiating a pairing operation between the patient bed and the pillow speaker according to the first wireless communication technology in response to selection of the pillow speaker ID on the GUI by a user. The pairing operation of the fourth aspect may include transmitting a bed ID of the patient bed to the handheld pillow speaker according to the first wireless communication technology. The method of the fourth aspect may further include transmitting the bed ID from the handheld pillow speaker to the nurse call system via a wired connection to establish a bed-to-room association between the patient bed and a room in which the patient bed ma bye located, and transmitting the bed ID and bed status data to the WAP of the network according to the second wireless communication technology.

In some embodiments, the first wireless communication technology of the fourth aspect may include Bluetooth technology. For example, the Bluetooth technology may include Bluetooth Low Energy (BLE) technology. Optionally, the method of the fourth aspect may further include transmitting audio signals between the patient bed and the handheld pillow speaker using the Bluetooth technology. The present disclosure also contemplates that the second wireless communication technology of the fourth aspect may comprise WiFi technology according to an 802.11 communication protocol.

Optionally, the method of the fourth aspect may further include establishing the wired connection from the handheld pillow speaker to the nurse call system by coupling a first connector of a cable extending from the pillow speaker to a second connector of a wall module of the nurse call system.

The method of the fourth aspect may further include sending a location ID from the wall module along with the bed ID for receipt by a nurse call server of the nurse call system and using the location ID, which corresponds to the room in which the patient bed is located, to establish the bed-to-room association. If desired, the handheld pillow speaker of the fourth aspect may include user inputs for (i) sending a nurse call signal to the nurse call system, (ii) controlling room lighting, and (iii) controlling at least one room entertainment device.

Optionally, the bed status data sent to the WAP of the network of the fourth aspect may include information regarding one or more of the following features of the patient bed: a frame position of a first portion of a frame of the patient bed relative to a second portion of the frame, inflation or deflation state of a bladder of a mattress supported by the frame, a siderail position of a siderail coupled to the frame, a caster brake status of one or more casters of the frame, an angle of a head section of the frame relative to horizontal or relative to another portion of the frame, whether a bed exit system of the patient bed may be armed, a patient weight detected using a weigh scale of the frame, or whether an upper frame portion of the frame may be in its lowest position relative to a base frame portion of the frame.

Further optionally, the bed status data sent to the WAP of the network of the fourth aspect may include information regarding one or more of the following alert conditions of the patient bed: a head section of a frame of the patient bed being lowered below a threshold angle relative to horizontal or relative to another portion of the frame, a siderail coupled to the frame being lowered, a patient exiting the patient bed, a patient moving to an unwanted position on the patient bed, an inability of a bladder of a mattress supported by the frame to be inflated to a target pressure, one or more casters of the frame becoming unbraked, an upper frame portion of the frame being moved out of its lowest position relative to a base frame portion of the frame, or a patient becoming incontinent on the patient bed.

In some embodiments, the method of the fourth aspect further may include sending at least some of the bed status data to the handheld pillow speaker according to the first wireless communication protocol. For example, the bed status data sent to the handheld pillow speaker of the fourth aspect may include information regarding one or more of the following features of the patient bed: a frame position of a first portion of a frame of the patient bed relative to a second portion of the frame, inflation or deflation state of a bladder of a mattress supported by the frame, a siderail position of a siderail coupled to the frame, a caster brake status of one or more casters of the frame, an angle of a head section of the frame relative to horizontal or relative to another portion of the frame, whether a bed exit system of the patient bed may be armed, a patient weight detected using a weigh scale of the frame, or whether an upper frame portion of the frame may be in its lowest position relative to a base frame portion of the frame.

The present disclosure also contemplates that the bed status data sent to the handheld pillow speaker of the fourth aspect may include information regarding one or more of the following alert conditions of the patient bed: a head section of a frame of the patient bed being lowered below a threshold angle relative to horizontal or relative to another portion of the frame, a siderail coupled to the frame being lowered, a patient exiting the patient bed, a patient moving to an unwanted position on the patient bed, an inability of a bladder of a mattress supported by the frame to be inflated to a target pressure, one or more casters of the frame becoming unbraked, an upper frame portion of the frame being moved out of its lowest position relative to a base frame portion of the frame, or a patient becoming incontinent on the patient bed.

In some embodiments, the patient bed of the fourth aspect may include a frame and a siderail that may be coupled to the frame and that may be movable between a raised position to block a patient from egressing from the patient bed and a lowered position to permit the patient to egress from the patient bed. The GUI of the fourth aspect may be pivotably coupled to the siderail.

Optionally, the method of the fourth aspect further may include transmitting a wireless nurse call signal from the patient bed according to the first wireless communication technology in response to a nurse call input of the patient bed being selected by a patient to send the nurse call signal, receiving the wireless nurse call signal at the handheld pillow speaker, and transmitting a wired nurse call signal from the handheld pillow speaker to the nurse call system. Alternatively or additionally, the handheld pillow speaker may include a second nurse call input that also may be selectable by the patient to send the wired nurse call signal to the nurse call system. If desired, the patient bed of the fourth aspect may include a frame and a siderail that may be coupled to the frame and that may be movable between a raised position to block a patient from egressing from the patient bed and a lowered position to permit the patient to egress from the patient bed. The nurse call input of the fourth aspect may be coupled to the siderail. In some embodiments, the method of the fourth aspect further includes changing a format of the wireless nurse call signal at the handheld pillow speaker to create the wired nurse call signal that is transmitted to the nurse call system.

Optionally, the method of the fourth aspect further may include receiving with the circuitry of the patient bed room number information that may be transmitted by the WAP according to the second wireless communication technology. Further optionally, the method of the fourth aspect further may include displaying a room number on the GUI of the patient bed based on the room number information received with the circuitry.

Additional features, which alone or in combination with any other feature(s), such as those listed above and those listed in the claims, may comprise patentable subject matter and will become apparent to those skilled in the art upon consideration of the following detailed description of various embodiments exemplifying the best mode of carrying out the embodiments as presently perceived.

BRIEF DESCRIPTION OF THE DRAWINGS

The detailed description particularly refers to the accompanying figures, in which.

DETAILED DESCRIPTION

Figure 1:
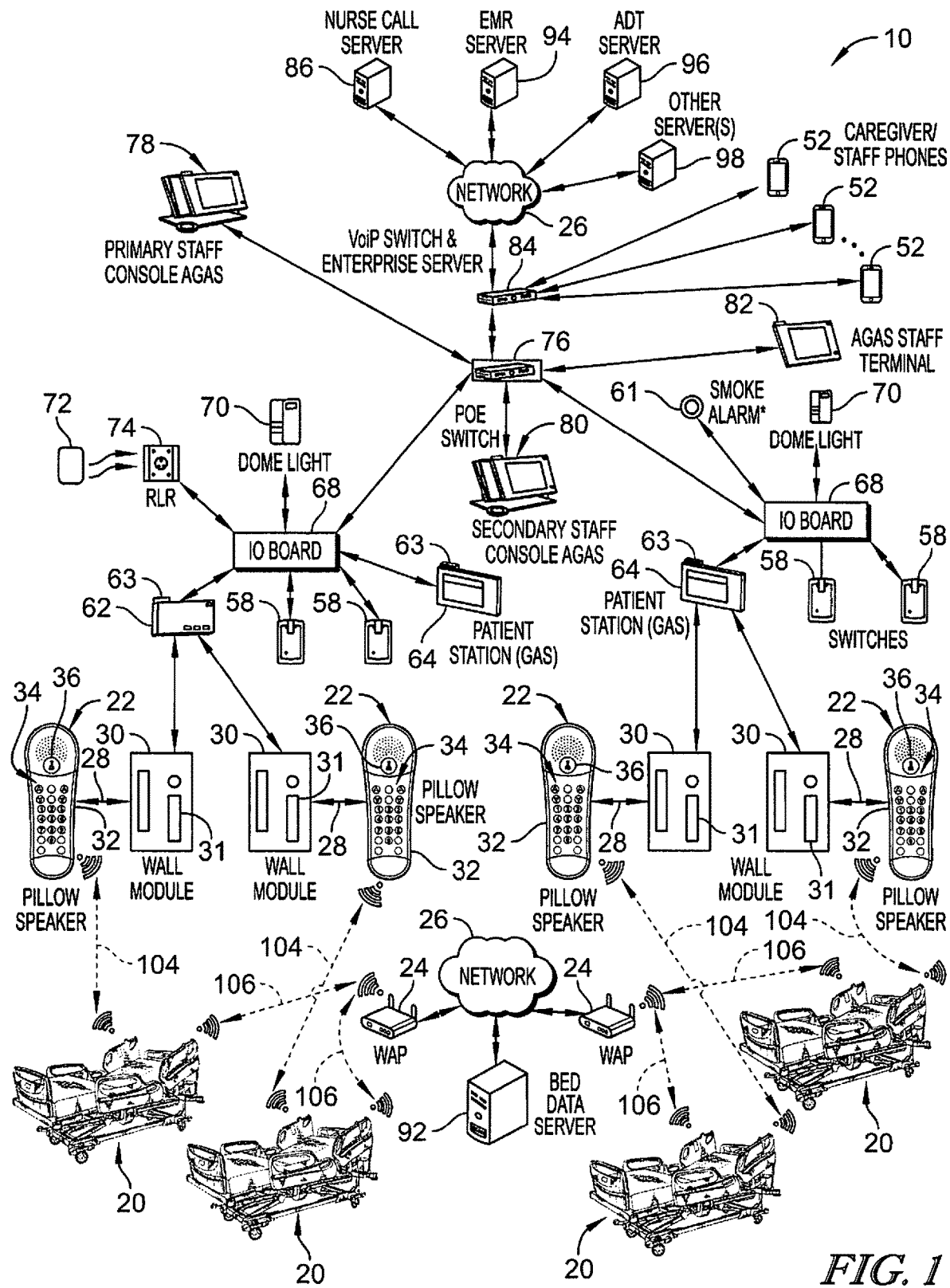
FIG. 1 is a block diagram of a portion of a network of a healthcare facility showing a number of patient beds communicating wirelessly with pillow speakers and with wireless access points (WAP's); the pillow speakers being coupled to wall modules of a nurse call system having patient stations, input/output boards, dome lights, primary staff stations, and secondary staff stations; and the nurse call system being in communication with other portions of the network via a Power over Ethernet (PoE) switch.

A healthcare information system 10 includes patient beds 20 that are configured to communicate wirelessly with respective handheld units such as illustrative pillow speakers 22 as shown in FIG. 1. Beds 20 are also configured to communicate wirelessly with one or more wireless access points (WAP's) 24 that are coupled to a network 26 of system 10. Beds 20 communicate wirelessly with pillow speakers 22 according to first and second wireless communication technologies that are different from each other and beds 20 also communicate wirelessly with WAP's according to a third wireless communication technology that is different from the first and second wireless communication technologies.

With regard to the first and second wireless communication technologies used for communications between beds 20 and respective pillow speakers 22, one is a short range wireless communication technology used for initially pairing the beds 20 with an accompanying one of the pillow speakers 22 and the other is a medium range wireless communication technology used to communicate data and audio between beds 20 and pillow speakers 22 after pairing. The third communication technology used for communications between beds 22 and WAP's 24 is a long range communication technology. The terms short range, medium range, and long range used in connection with wireless communications are relative terms in that medium range communications, for example, have a longer reception range than the short range communications and have a shorter reception range than the long range communications.

In the embodiments of beds 20 and pillow speakers 22 discussed in more detail below, the short range wireless communication technology comprises near field communication (NFC) technology, the medium range communication technology comprises Bluetooth (BT) technology, and the long range communication technology comprise Wireless Fidelity (WiFi) technology according to any of the 802.11 communications standards. NFC technology typically involves communication between electronic devices of about 4 centimeters (cm) (about 1½ inches) or less but can include communications up to about 10 cm (about 4 inches). The communication range of BT technology is generally dependent upon the power of the BT transmitter but BT devices include class 1 devices which are the most powerful and can operate up to about 100 meters (m) (about 330 feet), class 2 devices which are the most common type of BT devices and which can operate up to about 10 m (about 33 feet), and class 3 devices which don't typically operate beyond about 1 m (3.3 feet).

For BT communications between beds 20 and pillow speakers 22, the use of class 2 or class 3 BT devices suffice but this is not to rule out the possibility of using class 1 BT devices in beds 22 and pillow speakers 22. In the illustrative embodiment, Bluetooth Low Energy (BLE) is used as the medium range communication technology between beds 20 and pillow speakers 22. With regard to WiFi communication technology, if a traditional 2.4 gigahertz (GHz) band is used, the typical communication range for indoor applications is up to about 46 m (about 150 feet). In other embodiments, one or more of the first, second, and third wireless communication technologies used for wireless communications between beds 20 and handheld units 22, and between beds 20 and WAP's 24, are according to other technologies such as, for example, Zigbee; Z-wave; 6LoWPAN; Thread; WiFi-ah (HaLow); 2G (GSM); 3G; 4G; 5G; LTE Cat 0, 1 & 3; LTE-M1; NB-IoT; RFID; SigFox; LoRaWAN; Ingenu; Weightless-N; Weightless-P; Weightless-W; ANT & ANT+; DigiMesh; MiWi; EnOcean; Dash7; and WirelessHART; just to name a few.

Figure 2:
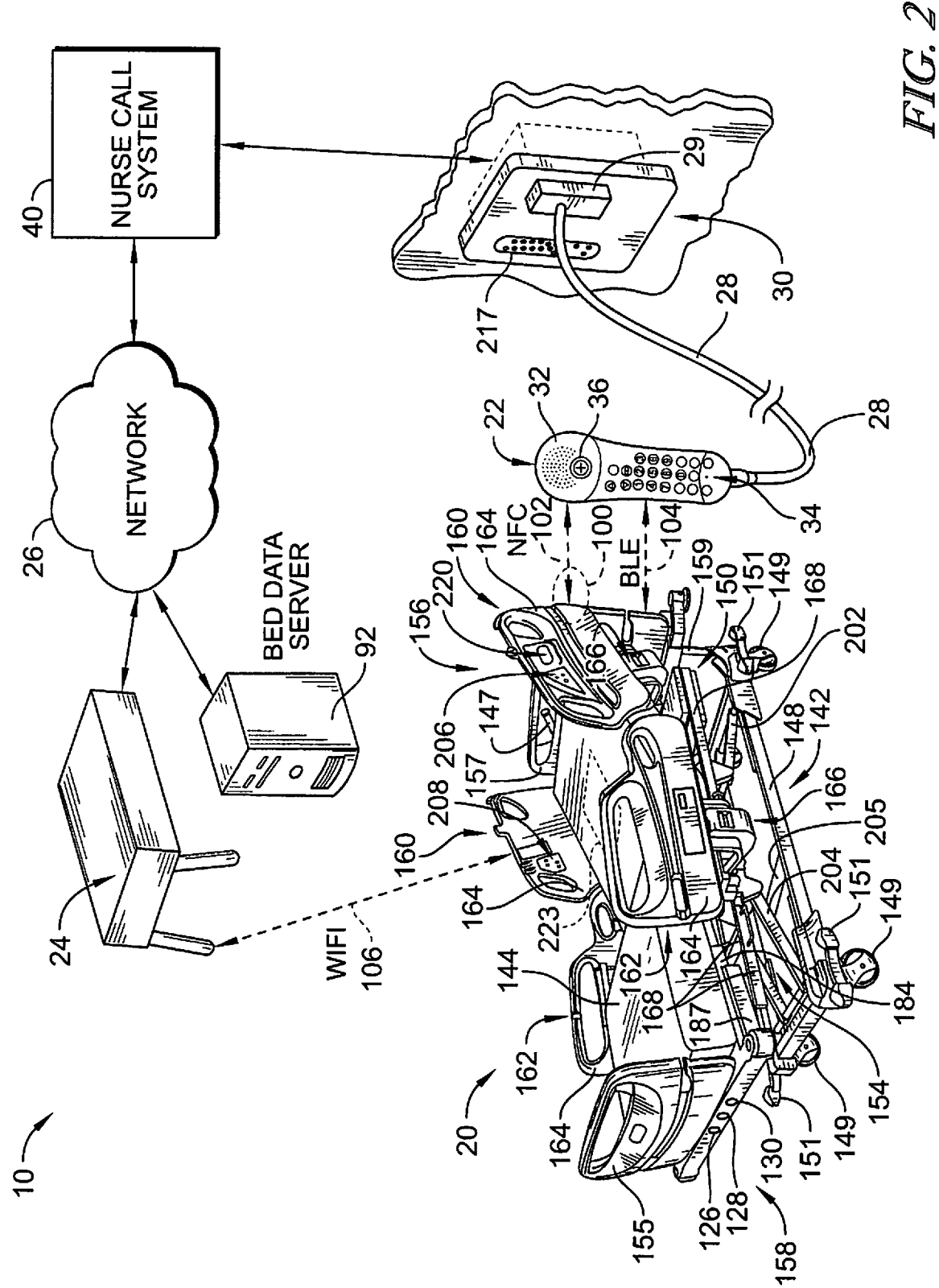
FIG. 2 is a perspective view showing a pillow speaker coupled to a respective wall module by a cable, a patient bed communicating with the pillow speaker using near field communication (NFC) and Bluetooth Low Energy (BLE) technologies, and the bed communicating with a WAP of the network using WiFi technology.

In the illustrative embodiment, pillow speakers 22 are coupled with appropriate cables 28 to respective wall modules 30 as shown diagrammatically in FIG. 1 and as shown in FIG. 2. The illustrative wall modules 30 comprise audio station bed connectors (ASBC's) 66 such as those available from Hill-Rom Company, Inc. In other embodiments, wall modules 30 may include one or more bed interface units (BIU's), network interface units (NIU's) or universal collectors (UC's) of the type that are also available from Hill-Rom Company, Inc. Further details of ASBC's, BIU's and NIU's are shown and described in U.S. Pat. Nos. 7,538,659 and 7,319,386 and in U.S. Patent Application Publication Nos. 2009/0217080 A1, 2009/0212925 A1 and 2009/0212926 A1, each of which is hereby expressly incorporated by reference herein to the extent not inconsistent with the present disclosure which shall control as to any inconsistencies. Further details of UC's are shown and described in U.S. Pat. No. 10,360,787 which is hereby expressly incorporated by reference herein in its entirety to the extent not inconsistent with the present disclosure which shall control as to any inconsistencies (see particularly FIGS. 11A-18 and the related discussion).

Each cable 28 terminates at a connector 29, shown for example in FIG. 2, that plugs into a mating connector 31 (see FIG. 1) of the respective wall module 30. In the illustrative example, connectors 29, 31 are 20-pin connectors (one male, one female) of the type provided in nurse call systems marketed by Hill-Rom Company, Inc. such as the COM-LINX®, COMPOSER®, and NAVICARE® nurse call systems. In nurse call systems marketed by other entities, connectors 29, 31 of system 10 are configured differently. For example, it is contemplated that system 10 may include any of the following styles of connectors 29, 31: 15-pin connectors of the type used in Amplion nurse call systems and SimplexGrinnell EZCARE® nurse call systems; 13-pin connectors of the type used in Dukane 2000, 2010, 2030, and 2070 nurse call systems; 18-pin connectors of the type used in Dukane ProCare 4000 and 6000, and System 2070 nurse call systems, as well as Ascom/GE TELLIGENCE® nurse call systems; 7-pin connectors of the type used in Executone Care/Com and Futura nurse call systems; 8-pin modular connectors of the type used in Critical Alert, Intego, TekTone, Wescom, and West-Com nurse call systems; 8-pin DIN connectors of the type used in Jeron Provider 680 and 790 nurse call systems as well as Rauland RESPONDER® III+, IV, and 4000 nurse call systems; 12-pin connectors of the type used in Rauland RESPONDER® III nurse call systems; 20-pin connectors of the type used in Sylvania/HCE nurse call systems; 10-pin modular connectors of the type used in some West-Com nurse call systems; and 9-pin D-sub connectors of the type used in Zettler Sentinel 500 nurse call systems; just to name a few.

Each pillow speaker 22 includes a housing 32 and a set of user inputs 34 on a front face of the housing 32. In the illustrative example, user inputs 34 are embodied as buttons or membrane switches that are manually pressed by a patient. One of buttons 34 is a nurse call button 36 that is used to send a nurse call signal to the nurse call portion of system 10. The other user inputs 34 are used to select television (TV) channels and to adjust the volume of the TV. In some embodiments, other ones of buttons 34 are used to make specific patient requests such as to request pain medication, water, and/or assistance in going to the bathroom. Still others of buttons 34 are used to turn on a room light or reading light in the patient room.

As its name implies, each pillow speaker 22 includes a speaker as part of the circuitry contained within housing 32. A set of small holes are provided on the front face of the housing 32 above nurse call button 36 in the general vicinity of the location of the speaker within housing 32. The speakers of pillow speakers 22 are used for TV sound and for communication with remote caregivers. In some embodiments, the speakers within housings 32 also serve as microphones and in other embodiments, separate microphones are included in the circuitry of pillow speakers 22. Pillow speakers 22, in some embodiments, are GEN4® DIRECT ACCESS® pillow speakers available from Curbell Medical Products, Inc. of Orchard Park, New York, or similar HILL-ROM® pillow speakers marketed by Hill-Rom Company, Inc. of Batesville, Indiana, but further equipped with NFC and/or BT/BLE wireless communication technologies as described herein. However, the present disclosure contemplates that other types of pillow speakers available from these same entities and from other manufacturers, and similarly modified to include wireless communication technologies as described herein, may be used in other embodiments of system 10 if desired.

Still referring to FIG. 1, other components of one possible architecture of system 10 are shown to provide context as to the type of healthcare communication system in which beds 20, handheld units 22, and wall modules 30 may be used. However, it should be appreciated that there are practically limitless ways in which healthcare facilities may choose to configure their network architecture. It should be further appreciated that, although FIG. 1 shows four beds 20, four pillow speakers 22, and four wall modules 30, a typical unit or wing of a healthcare facility will have more than four of these devices.

In the illustrative example, wall modules 30 are each coupled via appropriate cabling or wired communication links to either a standard audio station (SAS) 62 or a graphical audio station (GAS) 64. Each of audio stations 62, 64 includes a code blue call lever 63 which is pulled by a caregiver in an emergency such as when a patient in the room is having a heart attack. Pulling the code blue lever 63 results in a code blue emergency call message being sent to one or more caregivers for response. Other types of devices within the patient rooms, such as call switches 58 and smoke alarms 61 also result in emergency call messages being sent to one or more caregivers under appropriate circumstances (e.g., in response to one of the call switches 58 being pulled or otherwise activated or in response to detection of smoke by one of the smoke alarms 61).

Audio stations 62, 64 are each communicatively coupled to a respective input/output (I/O) circuit board 68 as shown diagrammatically in FIG. 1. Circuit boards 68 are each sometimes referred to herein as an I/O board or I/O circuitry. Each I/O board 68 includes a processor, such as a microprocessor, microcontroller, etc., that receives various alerts and calls, sometimes referred to herein as "alert messages," from beds 54, pillow speakers 22, smoke alarms 61, and audio stations 62, 64 in response to the code blue lever 63 being pulled, for example. The processor of I/O circuitry 68 determines an alert message priority designation for each of the incoming alert messages. For example, in the illustrative embodiment, alert messages are designated as either Normal alert messages or High Priority alert messages. However, in other embodiments, more than two alert message priority designations may be used. In some embodiments, use of nurse call buttons 36 of pillow speakers 22, code blue levers 63 of audio stations 62, 64, and smoke alarms from smoke alarm 61 each results in a High Priority alert message being sent, whereas use of buttons 34 of pillow speakers 22 to request pain medicine, water, or assistance going to the bathroom results in a Normal alert message being sent.

The I/O board 68 and therefore, the processor of I/O board 68, is located at the respective patient room. Thus, the alert message priority designation is made at each patient room for the alert messages being communicated to the I/O board 68 in some embodiments. As such, a central server is not needed for determining message priority for the messages received by each I/O board 68 but this is not to exclude the possibility that a central server (or really, any server remote from the patient room) may be used to determine alert message priority in other embodiments. The I/O board 68 forwards each alert message and its respective priority designation to the remainder of system 10.

Each I/O board 68 is coupled to a respective dome light 70 which really includes multiple lights that are illuminated to indicate room status. The illumination of the various lights of dome light 70 is controlled by the I/O board 68 based on alert conditions occurring in the respective patient room and based on caregiver presence in, or absence from, the respective patient room. Dome lights 70 are mounted outside each of the patient rooms, typically near (e.g., above) a doorway of the respective room. In some embodiments, I/O boards 68 are situated in a housing to which the dome lights 70 are mounted. Thus, the I/O boards 68 are located outside the patient rooms adjacent the dome lights 70 in such embodiments. In other embodiments, I/O boards 68 are located inside the patient rooms. In either case, the I/O boards are considered to be "at" the patient room according to this disclosure.

In the illustrative example, a locating badge 72 is shown in wireless communication with a remote locator receiver (RLR) 74 which, in turn, is communicatively coupled with a respective I/O board for the patient room in which the RLR 74 is located. It should be appreciated that system 10 includes a multitude of badges 72 that are worn by respective caregivers and a multitude of RLR's 74 located throughout the respective healthcare facility, including being located in the various patient rooms. In response to an RLR 74 detecting one or more badges 72 in any particular room, a signal or message is communicated to the respective I/O board 68 and the lighting of the associated dome light 70 is updated accordingly to indicate the presence of one or more caregivers in the respective patient room. In the illustrative example, badges 72 transmit infrared (IR) signals to RLR's 74 but alternative embodiments in which radio frequency (RF) transmissions, including ultra-wideband (UWB) transmissions, are made by badges 72 and/or RLR's 74 are within the scope of this disclosure.

Still referring to the diagrammatic example of FIG. 1, each I/O board 68 is communicatively coupled to a Power over Ethernet (PoE) switch 76 which is, in turn, communicatively coupled to a primary staff console 78 (sometimes referred to as a "master nurse station"), a secondary staff console 80, and a staff terminal 82. Information regarding the alert messages emanating from the various patient rooms are displayed on the primary staff console 78 and on the secondary staff console 78. In some embodiments, information regarding the alert messages is also displayed on a status board display (not shown) which is a large display screen located in the vicinity of the master nurse station at which the primary staff console 78 is located. For additional details of a suitable status board, see U.S. Pat. No. 8,779,924 which is hereby incorporated by reference herein for all that it teaches to the extent not inconsistent with the present disclosure which shall control as to any inconsistencies. In the illustrative example, PoE switch 76 is communicatively coupled to a voice over Internet protocol (VoIP) Switch and Enterprise server 84 which is, in turn, coupled to a nurse call server 86 via Ethernet infrastructure, illustrated diagrammatically as network 26 in FIG. 1.

Figure 3:
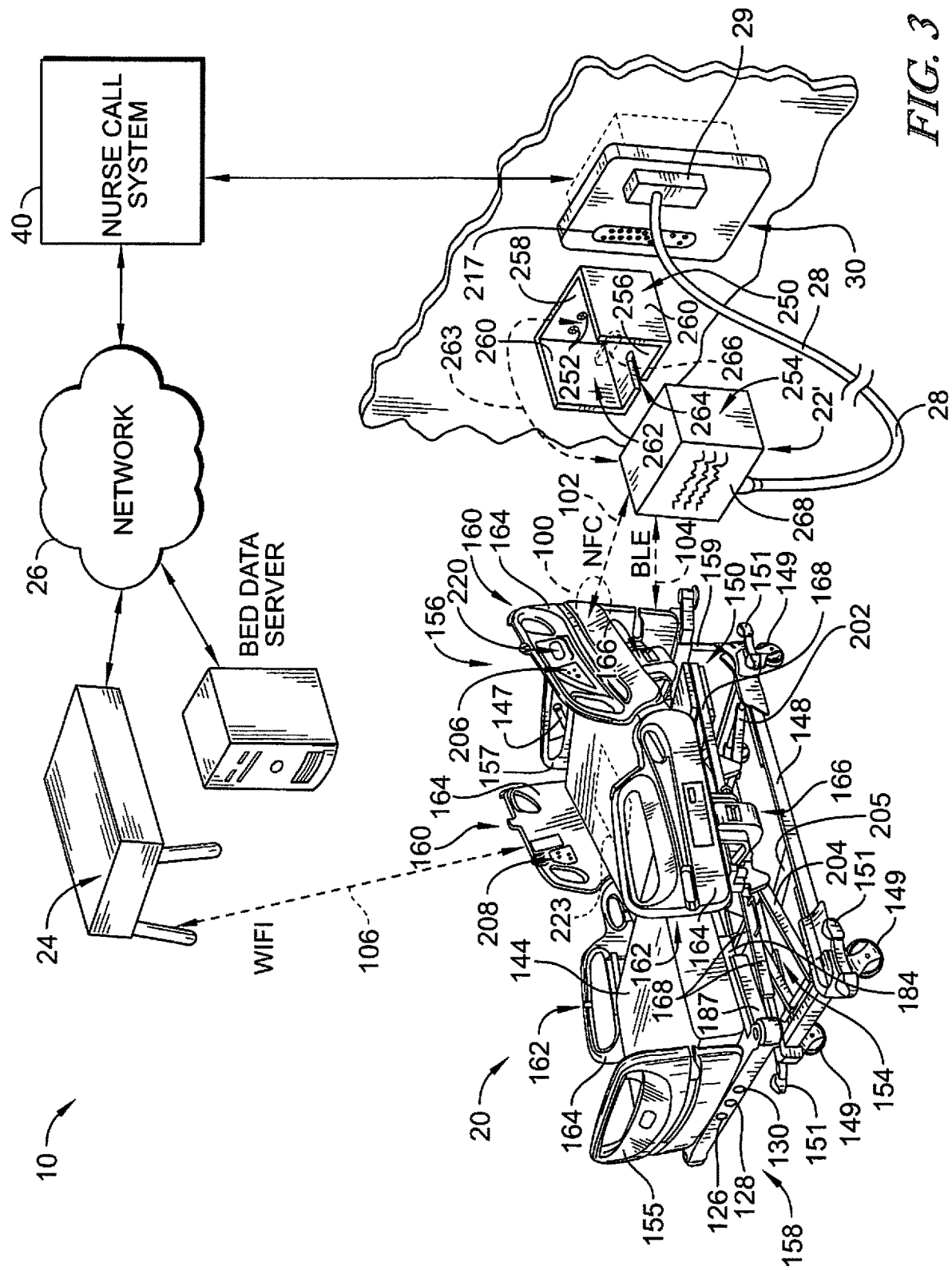
FIG. 3 is a perspective view, similar to FIG. 2, but showing a generic handheld unit or pairing module without any user inputs replacing the pillow speaker of FIG. 2 and showing a mount attached to a room wall to hold the handheld unit after the handheld unit has completed a pairing operation with the patient bed that occurs in response to the handheld unit being moved into a pairing zone adjacent a siderail of the patient bed.
Figure 9:
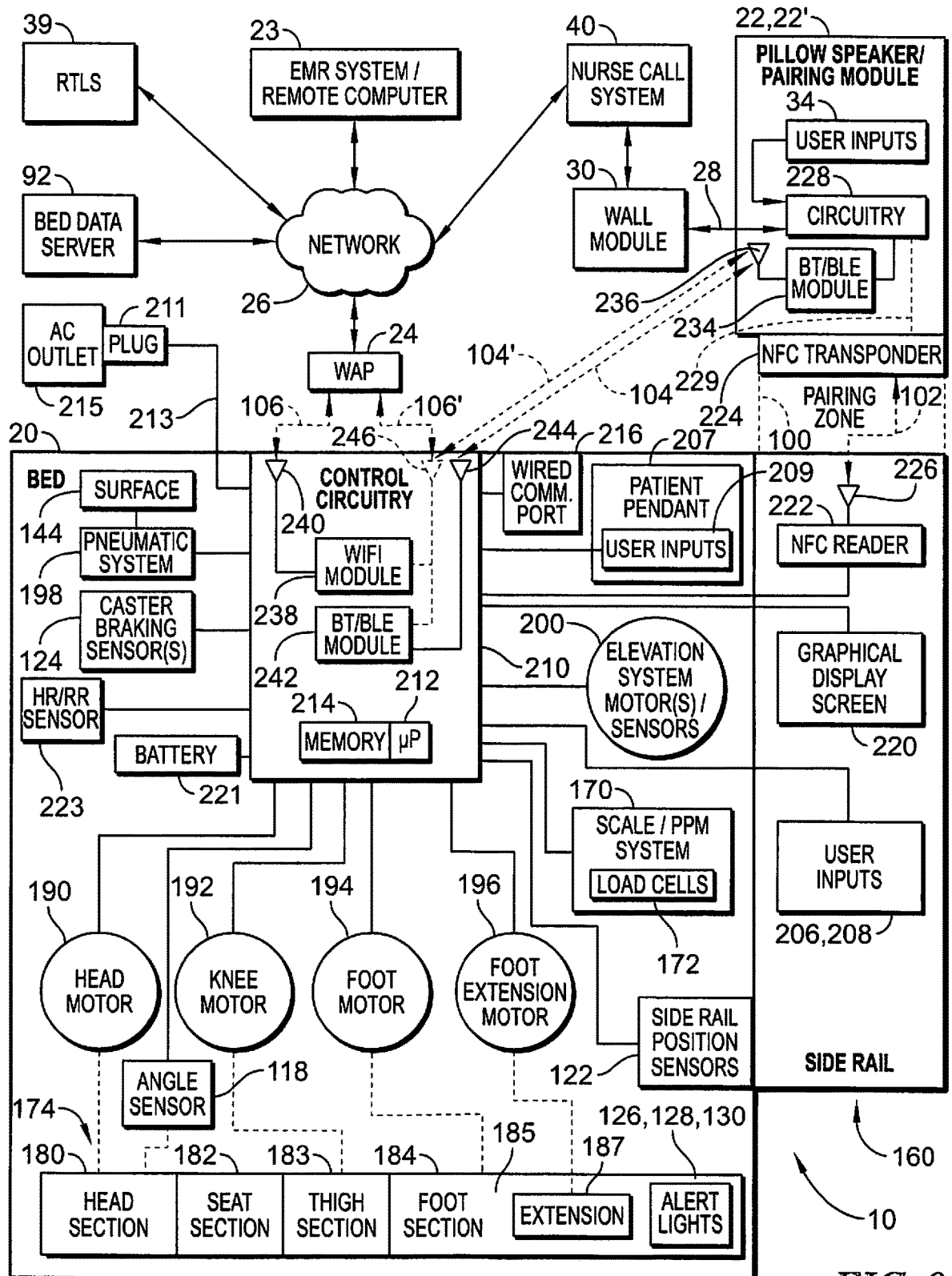
FIG. 9 is a block diagram showing various components of the patient bed, the pillow speaker or pairing module, and the network; the pillow speaker or pairing module having an NFC transponder attached thereto; the siderail of the patient bed having an NFC reader communicating wirelessly with the NFC transponder; and control circuitry of the patient bed having a Bluetooth (BT)/BLE module communicating wirelessly with a BT/BLE module of the pillow speaker or pairing module and having a WiFi module communicating wirelessly with the WAP.

It should be appreciated that devices 20, 22, 30, 58, 60, 62, 64, 66, 68, 70, 76, 78, 70, 82, 84, 86 are illustrative of a diagrammatic nurse call system portion of the overall system 10 and that nurse call system architecture will vary from one healthcare facility to the next. In FIGS. 2, 3 and 9, the diagrammatic box designated by reference number 40 is used to denote the portions of the nurse call system portion of overall system 10 that are not otherwise shown in these Figs. Other examples of nurse call system architecture and the various types of equipment included in various embodiments of a nurse call system (as well as network 10, in general) can be found in U.S. Pat. Nos. 7,746,218; 7,538, 659; 7,319,386; 7,242,308; 6,897,780; 6,362,725; 6,147,592; 5,838,223; 5,699,038 and 5,561,412 and in U.S. Patent Application Publication Nos. 2009/0217080; 2009/0214009; 2009/0212956; and 2009/0212925, each of which is hereby incorporated by reference herein in its entirety for all that it teaches to the extent not inconsistent with the present disclosure which shall control as to any inconsistencies.

In a similar way that portions of the nurse call system portion of overall system 10 are represented diagrammatically by box 40, an EMR system portion of overall system 10 is represented diagrammatically by a box 23 in FIG. 9. Thus, EMR system 23 includes EMR server 94 and the various remote computers of system 10 that are served by server 94 and that are configured with EMR software to access the patient electronic medical records stored in server 94 or in a separate EMR database computer or server and to enter data into the patient electronic medical records. Likewise, a real time locating system (RTLS) portion of overall system 10 is represented diagrammatically by a box 39 in FIG. 9. Thus, RTLS 39 includes an RTLS server (e.g., one of other servers 98 of FIG. 1), locating tags 72, receivers 74, and other locating and tracking equipment such as transceivers, local hubs, and remote computers for viewing locating and tracking information.

Illustrative system 10 includes a number of mobile devices 52, illustratively caregiver and staff mobile phones, that each operate a caregiver and staff communication software application for use in monitoring patient calls and alert messages originating from assigned patients and various hospital equipment located in a room of the patient, including patient beds 20, pillow speakers 22, and call switches 58, as shown in FIG. 1. In some embodiments, the caregiver and staff communication software application includes one or more software applications of the VOALTE® Mobile App and Platform such as the VOALTE® One, VOALTE® Me, VOALTE® Messenger, and VOATLE® Connect software marketed by Hill-Rom Company, Inc. The features and functions of the caregiver and staff communication software application of mobile devices 52 is discussed in further detail in U.S. Patent Application Publication No. 2019/0108908 A1 which is hereby incorporated by reference herein to the extent not inconsistent with the present disclosure which shall control as to any inconsistencies. The caregiver and staff communication software application is sometimes referred to herein as the mobile caregiver application.

In some embodiments, the mobile caregiver application is configured to allow caregivers in an acute care setting to use their mobile phones 52 for monitoring alerts and calls from patients; for conducting voice, video, and text messaging between caregivers; and for permitting voice communications to audio stations (e.g., standard audio stations 62 and/or graphical audio stations 64) mounted in patient rooms adjacent to respective patient beds 20. The mobile caregiver application is also configured to act as a secondary notification system that supplements the nurse call system 40 of overall system 10.

In connection with alert messages originating from beds 20, these include alert messages relating to one or more of the following: bed exit of the patient from the respective bed 54, patient position on the respective bed 54 exceeding a threshold, patient movement on the respective bed 54 exceeding a threshold or falling below a threshold, siderail position (e.g., siderail up or down) of the respective bed 54, casters of the respective bed 54 not being braked and/or being braked, angle of a head section of the respective bed 54 being below a threshold angle (e.g., 30 degrees), an upper frame of the respective bed 54 not being in its lowest position relative to a base frame of the respective bed 54, a bed component exceeding a threshold temperature, a mattress bladder of the respective bed 54 falling below a threshold pressure, a pneumatic system error or failure of the respective bed 54, an actuator error or failure of the respective bed 54, an overcurrent condition of a component of the respective bed 54, a power system error or failure of the respective bed 54, power being disconnected from the respective bed 54 (e.g., the bed being unplugged from a power receptacle), and battery charge status.

Still referring to FIG. 1, illustrative system 10 includes an electronic medical records (EMR) server 94 and an admission/discharge/transfer (ADT) server 96. System 10 includes various other servers 98 as well. Other servers 98 includes, for example, a real time locating system (RTLS) server that is communicatively coupled to receivers 74. In such embodiments, receivers 74 are not communicatively coupled to I/O boards 68 but rather communicate via network 26 with the RTLS server 98. The badges 72, receivers 74, and RTLS server 98 form a real time locating system portion of overall system 10 in such embodiments. Staff locating information is communicated from the RTLS server 98 to nurse call server 86 via network 26 in such embodiments.

In some embodiments, another of the other servers 98 is a server that manages the routing of alert messages and related staff information to the various mobile devices 52. In general, alert messages relating to particular patients or particular rooms assigned to particular caregivers are sent to the mobile device(s) 52 of the designated caregiver or caregivers. The alert messages may originate from beds 20, pillow speaker units 22, or even patient tablets in the some embodiments. For a discussion of the use of patient tablets to send alert messages or patient requests to caregivers, see U.S. application Ser. No. 16/857,291, filed Apr. 24, 2020, and titled "Patient Request System and Method," which is hereby incorporated by reference herein for all that it teaches to the extent not inconsistent with the present disclosure which shall control as to any inconsistencies. However, it is contemplated by this disclosure that alert messages originating from other types of equipment may be communicated to the mobile devices 52 of assigned caregivers as well.

The present disclosure further contemplates that system 10 includes a bed data server 92 which, in some embodiments, includes a database in which bed data from the various beds 20 of the healthcare facility is stored. In other embodiments, one or more separate computer devices are provided for storage of bed data and are coupled to bed data server 92 which manages the storage of bed data in such separate storage devices. Some of the bed data stored in the database associated with server 92 is also stored in nurse call server 86 and/or EMR server 94 in some embodiments. Optionally, the bed data server 92 and its associated database, whether included in server 92 or separate from server 92, may also store data from other types of medical devices (e.g., patient monitoring devices such as electrocardiograms (EKG's), electroencephalograms (EEG's), pulse oximeters, blood pressure monitors, respiration rate monitors, and temperature monitors, just to name a few; drug delivery devices such as drug infusion pumps; intravenous (IV) devices; ventilators; respiratory therapy devices such as devices for insufflation/exsufflation, oscillatory lung expansion (OLE), continuous positive expiratory pressure (CPEP), continuous high frequency oscillation (CHFO), continuous positive airway pressure (CPAP), Bi-PAP, and the like; compression therapy devices for treating deep vein thrombosis (DVT) including sequential compression devices (SCD's); and the like.

The data stored in bed data server 92 is used, in some embodiments, to calculate risk scores such as falls risk scores pertaining to the risk that a patient is likely to fall, pressure risk scores pertaining to the risk that a patient is likely to develop a decubitus ulcer (aka pressure sore), and a sepsis risk score pertaining to the risk that a patient is likely to develop sepsis. If desired, the risk scores are communicated to mobile devices 52 of caregivers. Thus, in some embodiments, bed data server 92 serves as an analytics engine for evaluating equipment and patient data to determine various risk scores, including modified early warning scores (MEWS), pediatric early warning scores (PEWS), Sepsis-Related Organ Failure Assessment (SOFA) scores, quick SOFA (qSOFA) scores, and System Inflammatory Response Syndrome (SIRS) scores, just to name a few. For additional details of the implementation of such an analytics engine with regard to server 92 and the display of various risk scores on mobile devices 52 of caregivers, see U.S. Patent Application Publication Nos. 2019/0336085 A1 and 2020/0066415 A1, each of which is hereby incorporated by reference herein for all that it teaches to the extent not inconsistent with the present disclosure which shall control as to any inconsistencies.

Referring now to FIG. 2, each bed 20 includes a patient support structure such as a frame 142 that supports a surface or mattress 144. It should be understood that FIG. 2 shows some details of one possible type of bed 20 used in system 10. However, this disclosure is applicable to other types of patient support apparatuses, including other types of beds, stretchers, chairs, wheelchairs, patient lifts and the like that are used to support a patient in a patient room. Illustrative beds 20 are CENTRELLA® beds available from Hill-Rom Company, Inc. but modified to include the NFC wireless communication technologies discussed herein. Other aspects of illustrative beds 20 are shown and described in more detail in U.S. Patent Application Publication No. 2018/0161225 A1 which is hereby expressly incorporated by reference herein to the extent not inconsistent with the present disclosure which shall control as to any inconsistencies. The discussion below of features of one of beds 20 is applicable to each of beds 20 unless specifically noted otherwise.

Still referring to FIG. 2, frame 142 of bed 20 includes a base frame 148 (sometimes just referred herein to as a base 148), an upper frame assembly 150 and a lift system 154 coupling upper frame assembly 150 to base 148. Lift system 154 is operable to raise, lower, and tilt upper frame assembly 150 relative to base 148. Bed 20 has a head end 156 and a foot end 158. Patient bed 20 further includes a footboard 155 at the foot end 158 and a headboard 157 at the head end 156. Illustrative bed 20 includes a pair of push handles 147 coupled to an upstanding portion 159 of base 148 at the head end 156 of bed 20. Only a portion of one push handle 147 can be seen in FIG. 1. Headboard 157 is coupled to upstanding portion 159 of base 148 as well. Foot board 155 is coupled to upper frame assembly 150. Base 148 includes wheels or casters 149 that roll along the underlying floor (not shown) as bed 20 is moved from one location to another. A set of foot pedals 151 are coupled to base 148 and are used to brake and release casters 149.

Illustrative patient bed 20 has four siderail assemblies coupled to upper frame assembly 150 as shown in FIG. 2. The four siderail assemblies include a pair of head end siderail assemblies 160 (sometimes referred to as head rails) and a pair of foot end siderail assemblies 162 (sometimes referred to as foot rails). Each of the siderail assemblies 160, 162 is movable between a raised position, as shown in FIG. 2, and a lowered position (not shown but well known to those skilled in the art). Siderail assemblies 160, 162 are sometimes referred to herein as just siderails 160, 162. Each siderail 160, 162 includes a barrier panel 164 and a linkage 166. Each linkage 166 is coupled to the upper frame assembly 150 and is configured to guide the barrier panel 164 during movement of siderails 160, 162 between the respective raised and lowered positions. Barrier panel 164 is maintained by the linkage 66 in a substantially vertical orientation during movement of siderails 160, 162 between the respective raised and lowered positions in the illustrative example of bed 20.

Upper frame assembly 150 includes various frame elements 168 that form, for example, a lift frame and a weigh frame supported with respect to the lift frame by a set of load cells 172 of a scale and/or patient position monitoring (PPM) system 170 which is shown diagrammatically in FIG. 9. A patient support deck 174, also shown diagrammatically in FIG. 9, is carried by the weigh frame portion of upper frame assembly 150 and supports mattress 144 thereon. Patient support deck 174 includes a head section 180, a seat section 182, a thigh section 183 and a foot section 184 in the illustrative example as shown diagrammatically in FIG. 9. Sections 180, 183, 184 are each movable relative to the weigh frame portion of upper frame assembly 150. For example, head section 180 pivotably raises and lowers relative to seat section 182 whereas foot section 184 pivotably raises and lowers relative to thigh section 183. Additionally, thigh section 183 articulates relative to seat section 182. Also, in some embodiments, foot section 184 is extendable and retractable to change the overall length of foot section 84 and therefore, to change the overall length of deck 174. For example, foot section 184 includes a main portion 185 and an extension 187 in some embodiments as shown diagrammatically in FIG. 9.

In the illustrative embodiment of bed 20, seat section 182 is fixed in position with respect to the weigh frame portion of upper frame assembly 150 as patient support deck 174 moves between its various patient supporting positions including a horizontal position to support the patient in a supine position, for example, and a chair position (not shown) to support the patient in a sitting up position. In other embodiments, seat section 182 also moves relative to upper frame assembly 150, such as by pivoting and/or translating. Of course, in those embodiments in which seat section 182 translates relative to the upper frame assembly 150, the thigh and foot sections 183, 184 also translate along with seat section 182. As bed 20 moves from the horizontal position to the chair position, foot section 184 lowers relative to thigh section 183 and shortens in length due to retraction of the extension 187 relative to main portion 185. As bed 20 moves from the chair position to the horizontal position, foot section 184 raises relative to thigh section 183 and increases in length due to extension of the extension 187 relative to main portion 185. Thus, in the chair position, head section 180 extends upwardly from upper frame assembly 150 and foot section 184 extends downwardly from thigh section 183.

As shown diagrammatically in FIG. 9, bed 20 includes a head motor or actuator 190 coupled to head section 180, a knee motor or actuator 192 coupled to thigh section 183, a foot motor or actuator 194 coupled to foot section 184, and a foot extension motor or actuator 196 coupled to foot extension 187. Motors 190, 192, 194, 196 may include, for example, an electric motor of a linear actuator. In those embodiments in which seat section 182 translates along upper frame assembly 150 as mentioned above, a seat motor or actuator (not shown) is also provided. Head motor 190 is operable to raise and lower head section 180, knee motor 192 is operable to articulate thigh section 183 relative to seat section 182, foot motor 194 is operable to raise and lower foot section 184 relative to thigh section 183, and foot extension motor 196 is operable to extend and retract extension 187 of foot section 184 relative to main portion 185 of foot section 184.

In some embodiments, bed 20 includes a pneumatic system 198 that controls inflation and deflation of various air bladders or cells of mattress 144. In FIG. 9, mattress 144 is shown diagrammatically in the block labeled as "SURFACE." The terms mattress and surface are used interchangeably herein. The pneumatic system 198 is represented diagrammatically in FIG. 9 as a single block but that block 198 is intended to represent one or more air sources (e.g., a fan, a blower, a compressor) and associated valves, manifolds, air passages, air lines or tubes, pressure sensors, and the like, as well as the associated electric circuitry, that are typically included in a pneumatic system for inflating and deflating air bladders of mattresses.

As also shown diagrammatically in FIG. 9, lift system 154 of bed 20 includes one or more elevation system motors or actuators 200, which in some embodiments, comprise linear actuators with electric motors. Thus, actuators 200 are sometimes referred to herein as motors 200. Alternative actuators or motors contemplated by this disclosure include hydraulic cylinders and pneumatic cylinders, for example. The motors 200 of lift system 154 are operable to raise, lower, and tilt upper frame assembly 150 relative to base 148. In the illustrative embodiment, one of motors 200 is coupled to, and acts upon, a set of head end lift arms 202 and another of motors 200 is coupled to, and acts upon, a set of foot end lift arms 204 to accomplish the raising, lowering and tilting functions of upper frame 150 relative to base 148. Guide links 205 are coupled to base 148 and to lift arms 204 in the illustrative example as shown in FIGS. 2 and 3.

Each of siderails 160 includes a first user control panel 206 coupled to the outward side of the associated barrier panel 164. Controls panels 206 include various buttons that are used by a caregiver to control associated functions of bed 20. For example, control panel 206 includes buttons that are used to operate head motor 190 to raise and lower the head section 180, buttons that are used to operate knee motor 192 to raise and lower the thigh section 183, and buttons that are used to operate motors 200 to raise, lower, and tilt upper frame assembly 150 relative to base 148. In some embodiments, control panel 206 also includes buttons that are used to operate motor 194 to raise and lower foot section 184 and buttons that are used to operate motor 196 to extend and retract foot extension 187 relative to main portion 185. Each of siderails 160 also includes a second user control panel 208 coupled to the inward side of the associated barrier panel 164. Controls panels 208 include various buttons that are used by a patient to control associated functions of bed 20. In some embodiments, the buttons of control panels 206, 208 comprise membrane switches that are used to control head motor 190 and knee motor 192.

As shown diagrammatically in FIG. 9, bed 20 includes control circuitry 210 that is electrically coupled to motors 190, 192, 194, 196 and to motors 200 of lift system 154. Control circuitry 210 is represented diagrammatically as a single block in FIG. 9, but control circuitry 210 in some embodiments, comprises various circuit boards, electronics modules, and the like that are electrically and communicatively interconnected. Control circuitry 210 includes one or more microprocessors 212 or microcontrollers that execute software to perform the various control functions and algorithms described herein. Thus, circuitry 210 also includes memory 214 for storing software, variables, calculated values, and the like as is well known in the art. The circuitry 210 may, therefore, include or be embodied as any device or circuitry (e.g., a processor, a microcontroller, a field programmable gate array (FPGA), an application specific integrated circuit (ASIC), reconfigurable circuitry, System on Chip (SoC), Programmable System on Chip (PSoC), Computer on Module (CoM), and System on Module (SoM), etc.) and/or software configured to operate the bed 20 as described herein. In some embodiments, circuitry 210 includes a model no. VAR-SOM-MX6 System on Module (SoM) available from Variscite Ltd. of Lod, Israel that serves as or is provided on a Master Control Board (MCB) of bed 20.

As also shown diagrammatically in FIG. 9, a user inputs block 206, 208 represents the various user inputs such as buttons of control panels 206, 208, for example, that are used by the caregiver or patient to communicate input signals to control circuitry 210 of bed 20 to command the operation of the various motors 190, 192, 194, 196, 200 of bed 20, as well as commanding the operation of other functions of bed 20. Bed 20 includes at least one graphical user input (GUI) or display screen 220 coupled to a respective siderail 160 as shown in FIGS. 2, 3 and 5-8. Display screen 220 is coupled to control circuitry 210 as shown diagrammatically in FIG. 9. In some embodiments, two graphical user interfaces 220 are provided and are coupled to respective siderails 160. Alternatively or additionally, one or more graphical user interfaces are coupled to siderails 162 and/or to one or both of the headboard 157 and footboard 155. Control circuitry 210 receives user input commands from graphical display screen 220.

In the illustrative embodiment, bed 20 has a communication interface or port 216, shown diagrammatically in FIG. 9, which optionally provides bidirectional communication with wall module 30 via a nurse call cable (not shown), such as a nurse call cable having 37-pin connectors at its ends of the type available from Hill-Rom Company, Inc. As shown in FIGS. 2 and 3, wall module 30 includes a port 217 configured for coupling with one of the 37-pin connectors of the nurse call cable. However, the present disclosure contemplates that the nurse call cable between port 216 of bed 20 and port 217 of wall module 30 is omitted and that data and audio that normally is communicated over the nurse call cable, when present, is instead communicated via BLE wireless communications between bed 20 and pillow speaker 22. Wall module 30, in turn, communicates bidirectionally with the remainder of nurse call system 40.

Still referring to FIG. 9, illustrative bed 20 includes a patient pendant 207 with user inputs 209, such as buttons or membrane switches that are used by a patient to control features of bed 20 via signals sent to control circuitry 210. In some embodiments, the user inputs 209 of patient pendant 207 are the same as the user inputs 208 on one or both of siderails 160, although this is not to rule out the possibility that the user inputs 209 of patient pendant 207 may be used to control more or less functions of bed 20 than user inputs 208. Bed 20 further includes a standard alternating current (AC) power plug 211 at a terminal end of a power cord 213. Plug 211 plugs into a standard AC receptacle or outlet 215 as shown diagrammatically in FIG. 9. Bed 20 further includes a battery 221 that provides power to various electrical components of bed 20 when plug 211 is unplugged from AC power. In some embodiments, battery 221 recharges in response to plug 211 being plugged into the AC outlet 215. Optionally, bed 20 includes a heartrate (HR) and/or respiration rate (RR) sensor 223 as shown in FIGS. 2, 3 and 9. Sensor 223 is situated between mattress 144 and head section 180 in some embodiments. For example, sensor 223 is a Contact-Free Sensor available from EarlySense Inc. of Ramat Gan, Israel ins some embodiments. Sensor 223 provides HR and/or RR signals to control circuitry 210 via the associated electrical connection shown diagrammatically in FIG. 9.

As shown diagrammatically in FIG. 2, a pairing zone 100 exists adjacent to one of head end siderails 160. In some embodiments, pairing zone 100 exists adjacent to both of head end siderails 160 such that pairing zones 100 are provided on both sides of bed 20. The size of pairing zone 100 is defined by the reception range of the NFC technology used for wireless communications between bed 20 and handheld unit 22. As noted above, the reception range of NFC technology is about 4 centimeters (cm) (about 1½ inches) to about 10 cm (about 4 inches). In FIG. 2, an NFC wireless communication link 102 and a BLE wireless communication link 104 are shown diagrammatically between bed 20 and pillow speaker 22 and a WiFi wireless communication link 106 is shown diagrammatically between bed 20 and WAP 24. It should be appreciated that NFC link 102 is exaggerated in size in FIG. 2 and that, in reality, communication link 102 only exists when pillow speaker 22 is within pairing zone 100. That is, pillow speaker 22 must be moved to a position close enough to siderail 160 to be within the pairing zone 100 before link 102 is established between bed 20 and pillow speaker 22. It should also be appreciated that, in some circumstances, wireless communication links 106 may be established between bed 20 and multiple WAP's 24 if bed is within reception range of multiple WAP's 24.

As shown diagrammatically in FIG. 9, an NFC reader 222 is carried by siderail 160 and an NFC transponder 224 is attached to pillow speaker 22. NFC reader 222 includes an antenna 226 that reads data emitted from NFC transponder 224, including a transponder ID. It is known that NFC operates at a frequency of about 13.56 megahertz (MHz) on ISO/IEC 18000-3 air interface and at data transfer rates from about 106 kilobits per second (kbits/s) to about 424 kbits/s. In the illustrative example, NFC reader 222 is electrically coupled to circuitry 210 and receives power therefrom. In some embodiments, transponder 224 is an active transponder 224 which is electrically coupled to circuitry 228 of pillow speaker 22 as indicated by dashed line 229. In such embodiments, therefore, reader 222 and transponder 224 are both powered such that bidirectional, peer-to-peer communication is achieved therebetween via the NFC wireless communication link 102.

In other embodiments, transponder 224 is passive such that NFC reader 222 serves as an initiator circuit with transponder 224 being a passive target. In such embodiments, the electrical coupling 229 between NFC transponder 224 and circuitry 228 is omitted. Also in such embodiments, the initiator 222 actively generates a radio frequency (RF) field from antenna 226 that powers the passive transponder 224 and transponder 224 responds by emitting data that is received by antenna 226. In such alternative arrangements, the passive transponder 224 can be fashioned as a tag, a sticker, a fob, or a card that lacks any battery or other connection to external power sources. According to this disclosure, transponder 224 preferably includes a transponder chip (e.g., integrated circuit chip) and an antenna that are included in a label that sticks to a back surface of the housing 32 of pillow speaker 22. In still other embodiments, transponder 224 is an active transponder that includes its own battery.

When pillow speaker 22 is brought into close proximity with siderail 160 so that transponder 224 enters into pairing zone 100, the reader 222 automatically establishes communications in roughly about one tenth of a second with transponder 224. Due to the short reception range between antenna 226 of reader 222 and transponder 224, the likelihood of unwanted interference from other wireless signals is reduced. In some embodiments, NFC reader 222 includes a model no. TRF7970A transceiver available from Texas Instruments of Dallas, Texas In embodiments in which transponder 224 is an active transponder, then transponder 224 also may include a model no. TRF7970A transceiver available from Texas Instruments. Passive NFC labels including passive transponders 224 are available from any number of manufacturers including, for example, NXP of Eindhoven, Netherlands; Confidex Ltd. of Tampere, Finland; Alpha Card Systems LLC of Portland, Oregon; and Zebra Technologies Corp. of Lincolnshire, Illinois; just to name a few.

The NFC transponder 224 attached to pillow speaker 22 is programmable such that any desired identification (ID) data can be written into memory of the transponder 224 for subsequent transmission when energized by reader 222. If desired, for example, the transponder 224 can be programmed with a serial number of the handheld unit 22, a MAC address of the handheld unit 22, or any other transponder ID.

Figure 10:
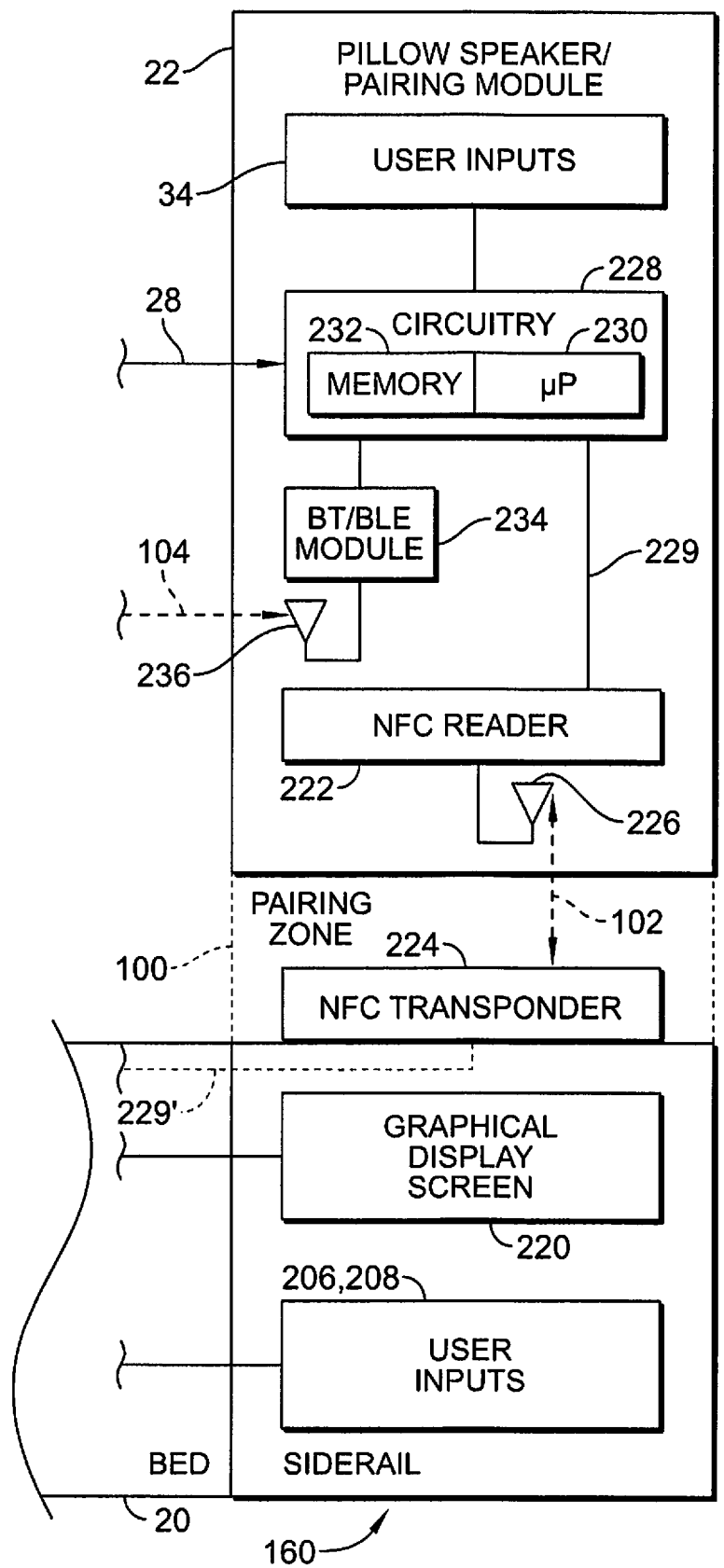
FIG. 10 is a block diagram showing an alternative embodiment of a portion of the components depicted in FIG. 9, the alternative embodiment having an NFC transponder coupled to the siderail of the patient bed and the pillow speaker or pairing module having an NFC reader in wireless communication with the NFC transponder.

As shown in FIG. 10, in an alternative embodiment, transponder 224 is attached to siderail 160 and pillow speaker 22 carries NFC reader 222 and its associated antenna 226. Thus, in the alternative embodiment, when pillow speaker 22 is moved into pairing zone 100, the NFC wireless communication link 102 is established between NFC reader 222 of pillow speaker 22 and NFC transponder of bed 20. The electrical connection 229 between circuitry 228 of pillow speaker 22 and reader 222 is shown in solid line in FIG. 10 since reader 222 receives its power from circuitry 228. The discussion above of reader 222, transponder 224, and antenna 226 in connection with FIG. 9 is equally applicable to these components in FIG. 10 except that the locations of these components is reversed. If NFC transponder 224 attached to siderail 160 is an active transponder, then an electrical connection to circuitry 210 is provided as indicated by dashed line 229' in FIG. 10.

FIG. 10 also shows that circuitry 228 of pillow speaker 22 includes a microprocessor 230 and memory 232. Alternatively or additionally, the circuitry 228 of pillow speaker may include or be embodied as any device or circuitry (e.g., a processor, a microcontroller, a field programmable gate array (FPGA), an application specific integrated circuit (ASIC), reconfigurable circuitry, System on Chip (SoC), Programmable System on Chip (PSoC), Computer on Module (CoM), and System on Module (SoM), etc.) and/or software configured to operate the pillow speaker 22 as described herein. As also shown in FIGS. 9 and 10, pillow speaker 22 includes a BT and/or BLE (aka BT/BLE) module 234 which includes an associated antenna 236.

Circuitry 210 of bed 20 includes a WiFi module 238 having an antenna 240 and a BT/BLE module 242 having an antenna 244. WiFi module 238 controls communications from bed 20 to WAP 24 over communication link 106 and BT/BLE module 242 controls communications from bed 20 to BT/BLE module 234 of handheld unit 22. Of course communication links 104, 106 are each bidirectional communication links and so module 238 also receives incoming communications from WAP 24 and module 242 receives incoming communications from module 234. In alternative embodiments, modules 238, 242 are combined together and share a single antenna 246 for wireless communications with WAP 24 and with BT/BLE module 234. Such an alternative configuration is found, for example, in SOM's available from Variscite Ltd. of Lod, Israel. In FIG. 9, an alternative bidirectional BT/BLE wireless communication link 104' is shown between antenna 246 and antenna 236 of module 234 of pillow speaker 22 and an alternative bidirectional WiFi wireless communication link 106' is shown between antenna 246 and WAP 24. The combined module 238, 242 implements a time division multiple access (TDMA) scheme so that antenna 246 transmits and receives according to the 802.11 protocol for WiFi communications 106' at certain times and so that antenna 246 transmits and receives according to the Bluetooth or Bluetooth Low Energy protocol for BT/BLE communications 104' at other times.

In connection with establishing BT/BLE pairing between module 234 of pillow speaker 22 and module 238 of bed 20 in the FIG. 9 embodiment having NFC reader 222 on bed 20, the transponder ID received by reader 222 from transponder 224 is communicated to circuitry 210 of bed 20 and stored in memory 214. The BT/BLE module 242 then broadcasts a BT/BLE message that includes the transponder ID and a bed ID. The bed ID includes, for example, the bed serial number or bed MAC address or some other ID that identifies bed 20 or module 242 of bed 20. Module 234 of pillow speaker 22 receives the broadcast message from module 242 of bed 22 and recognizes that the message includes the transponder ID corresponding to the NFC transponder 224 attached to the pillow speaker 22. Module 234 then responds by transmitting a pillow speaker ID that may include be, for example, the serial number of the pillow speaker 22, a MAC address of the circuitry 228 or module 234 of pillow speaker 22, or even the transponder ID may be used as the pillow speaker ID transmitted from module 234. Module 234 also transmits the bed ID back to the bed 20. After the modules 234, 242 have exchanged the relevant ID's, the modules 234, 242 enter into a paired state for data transfer over communication link 104 or communication link 104' as the case may be.

In connection with establishing BT/BLE pairing between module 234 of pillow speaker 22 and module 238 of bed 20 in the FIG. 10 embodiment having NFC reader 222 on pillow speaker 22, the transponder ID received by reader 222 from transponder 224 is communicated to circuitry 228 of pillow speaker 22 and stored in memory 232. The BT/BLE module 234 then broadcasts a BT/BLE message that includes the transponder ID and a pillow speaker ID that may be, for example, the serial number of the pillow speaker 22 or a MAC address of the circuitry 228 or module 234 of pillow speaker 22. Module 242 of bed 20 receives the broadcast message from module 234 of pillow speaker 22 and recognizes that the message includes the transponder ID corresponding to the NFC transponder 224 attached to the bed 20. Module 242 then responds by transmitting a bed ID that may be, for example, the serial number of the bed 20, a MAC address of the circuitry 210 or module 242 of bed 20, or even the transponder ID may be used as the bed ID transmitted from module 242. Module 242 also transmits the pillow speaker ID back to the pillow speaker 22. After the modules 234, 242 have exchanged the relevant ID's, the modules 234, 242 enter into a paired state for data transfer over communication link 104 or communication link 104' as the case may be.

Still referring to FIG. 9, bed 20 includes various sensors to sense the states or positions of various portions of bed 20. In the illustrative example, bed 20 includes an angle sensor 118 coupled to head section 180 to sense an angle of head section elevation (sometimes referred to as the head-of-bed (HOB) angle). Angle sensor 118 is an accelerometer (single-axis or multi-axis) in some embodiments. In such embodiments, the HOB angle is measured with respect to a horizontal reference axis and/or with respect to a vertical reference axis depending upon the orientation of the accelerometer relative to head section 180 and depending upon the type of accelerometer used. In other embodiments, angle sensor 118 includes a rotary potentiometer which measures the HOB angle between head section 180 and another portion of frame 142 such as one of frame members 168 of upper frame assembly 50. In further embodiments, angle sensor 118 is included in head motor 190 and has an output that correlates to the HOB angle. Motor 190 may include, for example, a shaft encoder, a Hall effect sensor, a rotary potentiometer, or some other sensor which serves as angle sensor 118 of bed 20 in such embodiments. Similar such sensors are included in elevation system motors 200 in some embodiments and are used to determine the position of upper frame assembly 150 relative to base 148 such as the height of upper frame assembly 150 and/or amount of tilt of upper frame assembly 150 relative to base 148.

Bed 20 also includes siderail position sensors 122 to sense the position (e.g., raised and/or lowered) of each of siderails 160, 162 and one or more caster braking sensors 124 to sense whether casters 149 are braked or released. In some embodiments, sensors 122, 124 include limit switches that are engaged or disengaged by a linkage mechanism, such as linkage 166 in the case of siderails 160, 162, to produce output signals indicative of the position of the respective mechanical structure. Alternatively, Hall effect sensors may be used as some or all of sensors 122, 124 in some embodiments. The foregoing types of sensors 122, 124 are just a couple examples of suitable sensors and therefore, this disclosure is intended to cover all types of sensors that may be used as sensors 122, 124. Each of the sensors mentioned above, including sensors internal to motors 190, 200 and sensors 118, 122, 124 are each coupled electrically to control circuitry 210 for analysis and/or processing of the signals therefrom.

In some embodiments, bed 20 has safety protocol capability. Thus, control circuitry 210 is programmed to enable and disable the safety protocols of bed 20. In the illustrative embodiment discussed herein, control circuitry 210 of bed 20 is configured to implement three different safety protocols, namely, a falls risk protocol (aka a falls protocol), a pulmonary protocol, and a safe skin protocol (aka a skin protocol). It should be understood that these are just examples of possible protocols for implementation on bed 20 and other protocols based on bed status information are within the scope of this disclosure. Additional details of the falls risk, pulmonary, and safe skin protocols can be found in U.S. Pat. No. 10,561,549 which is hereby incorporated by reference herein in its entirety to the extent not inconsistent with the present disclosure which shall control as to any inconsistencies.

As shown in FIGS. 2 and 3, illustrative bed 20 includes three status or alert lights 126, 128, 130 at foot end 158 corresponding to three monitored features of bed 20. In other embodiments, more or less than three alert lights are provided at the foot end 158 of bed 20. In the illustrative example, alert light 126 pertains to siderail position status, alert light 128 pertains to a bed exit status of the scale/PPM system 170, and alert light 130 pertains to bed height status. Also in the illustrative example, alert lights 126, 128, 130 are coupled to a lateral frame member of extension 187 of foot section 184 and are situated beneath footboard 155. In other embodiments, alert lights 126, 128, 130 may be located elsewhere on bed 12 such as on base 148 and/or one or more of siderails 160, 162. In FIG. 9, alert lights 126, 128, 130 are represented diagrammatically as a single block. It should be appreciated that alert lights 126, 128, 130 are coupled electrically to control circuitry 210 which is programmed to control the manner in which alert lights 126, 128, 130 are illuminated as will be discussed in further detail below. However, a diagrammatic electrical line from the block representing alert lights 126, 128, 130 to control circuitry 210 is omitted from FIG. 9 due to space constraints.

With regard to alert light 126, bed 20 is programmable by a caregiver using GUI 220 to monitor the status of one, two, three, or four of siderails 160, 162 being in a raised position. For example, it may be desirable for both of siderails 160 to be in raised positions but siderails 162 do not necessarily also need to be in raised positions. Alternatively, if one side of bed 20 is up against a room wall, then it may be desirable for only one of siderails 160 (e.g., the one away from the room wall) to be raised. If the patient is a high fall risk, the it may be desirable for all four of siderails 160, 162 to be raised. With regard to alert light 128, bed 20 is programmable by a caregiver using GUI 220 or control panel 206 select whether the bed exit or PPM system 170 of bed 20 is armed or enabled in one of three different levels of sensitivity for alarming in response to a patient moving into an unwanted position such as moving toward exiting the bed 20 or actually exiting the bed 20. With regard to alert light 130, bed 20 is programmable by a caregiver using GUI 220 or control panel 206 to monitor whether upper frame assembly 150 is in its lowest position relative to base frame 148.

Alert lights 126, 128, 130 are illuminated different colors to indicate certain statuses. For example, lights 126, 128, 130 are turned off if the particular status or feature is not being monitored. Lights 126, 128, 130 are illuminated a first color, such as green for example, if the associated monitoring of the corresponding feature is enabled, meaning the bed statuses contributing to the particular features are being monitored for a protocol violation, but all of the monitored bed statuses for the particular feature are satisfactory or in a desirable state (i.e., not violated). Lights 126, 128, 130 are illuminated a second color, such as amber or yellow for example, if the associated monitoring of the feature is enabled and at least one of the monitored bed statuses for the particular feature is undesirable or unsatisfactory (i.e., violated). In some embodiments, an audible alarm of bed 20 may also sound under the control of control circuitry 210 if an unsatisfactory condition of a particular monitored feature is detected. In some embodiments, one or more of lights 126, 128, 130 are illuminated a third color, such as blue for example, if the associated monitoring of the feature is enabled and at least one of the monitored bed statuses for the particular feature is undesirable (i.e., violated), but the alert has been suspended by a caregiver via appropriate user inputs on GUI 220 or control panel 206. If a particular alert has been suspended, any associated audible alarms may be turned off during the alarm suspension.

In some embodiments, alert lights 126, 128, 130 may be illuminated the second color, yellow for example, continuously in response to an unsatisfactory condition of the associated protocol being detected and may flash on and off in the second color if the alert has been suspended. Alternatively, alert lights 126, 128, 130 may be flashed on and off in the second color, yellow for example, in response to an unsatisfactory condition of the associated protocol being detected and may be illuminated continuously in the second color if the alert has been suspended. In such embodiments, therefore, lights 126, 128, 130 are not illuminated in any third color to indicate the suspension of the alarm of the associated protocol.

With regard to FIG. 9, it should be noted that not all electrical components of bed 20 are intended to be shown. For example, pneumatic system 198 is depicted by a single block which is intended to represent associated electrical components such as electrically operated valves, including solenoid valves, and air sources, such as blowers, compressors, and pumps. Power circuitry such as the components that receive AC power via cable 213 from the external AC power outlet 215 and convert the received power to appropriate DC voltage levels, such as 5 V for powering integrated circuit components and 24 V for powering the bed motors and actuators, are omitted from FIG. 9. Furthermore, while FIG. 9 diagrammatically uses a single block to represent control circuitry 210 and includes a single microprocessor 212 and memory 214 represented by respective blocks, this is not intended to imply that all of control circuitry 210 is on a single circuit board or that circuitry 210 has only one microprocessor or one memory component. In some embodiments, bed 20 has multiple circuit boards carried by various portions of frame 142 and has multiple microprocessors 212 and memory devices 214 as well as additional accompanying circuit components.

As noted above, pillow speaker 22 is moved into pairing zone 100 to permit NFC wireless communications 102 to be established between bed 20 and pillow speaker 22 and thereafter, BT/BLE pairing occurs so that BT/BLE wireless communications link 104 is established between bed 20 and pillow speaker 22. In an alternative embodiment shown in FIG. 3, a generic handheld unit or pairing module 22' is moved into pairing zone 100 so that NFC wireless communications 102 is established between bed 20 and pairing module 22' and thereafter, BT/BLE pairing occurs so that BT/BLE wireless communications link 104 is established between bed 20 and pairing speaker 22'. Basically, pairing module 22' includes the same internal components (e.g., circuitry 228, processor 230, memory 232, BT/BLE module 234, antenna 236, and optionally, NFC reader 222 and antenna 226) as pillow speaker 22 but the user inputs 34 that are present on pillow speaker 22 are absent from pairing module 22'. Thus, pairing module 22' is devoid of any manual user inputs. In some embodiments, pairing module 22' includes NFC transponder 224 of the type described above coupled thereto.

In use, pillow speaker 22 is held by a patient supported on bed 20 or is placed on mattress 144 next to the patient so as to be available to the patient for use when needed. It is also not uncommon for cable 28 extending from pillow speaker 22 to be tied into a loose knot around a hand grip portion of one of siderails 160 so that the pillow speaker 22 hangs from the siderail 160 at a location accessible to the patient. However, in the case of pairing module 22', there is really no reason for the patient to have access to it while on the bed 20, or at any time for that matter. Thus, a mounting bracket 250 is attached to the room wall, such as with screws 252, and is configured to support pairing module 22' before and after the pairing operation between bed 20 and pairing module 22'.

In the illustrative example, pairing module 22' has a cube-shaped housing 254 and mounting bracket has a bottom wall 256, a back wall 258, and a pair of spaced apart sidewalls 260 that form a pocket 262 that receives pairing module 22'. Thus, mounting bracket 250 is open at its top and front to permit pairing module 22' to be selectively inserted into and removed from mounting bracket 250 as indicated by dotted double headed arrow 263. A slot 264 is provided in bottom wall 256 to accommodate cable 28 which extends downwardly from a bottom of housing 254 of pairing module 22'. Slot 264 is located about midway between side walls 260 and is open at its front. Optionally, a retainer 266 is provided on mounting bracket 250 to retain pairing module 22' in pocket 262. In the illustrative example, retainer 266 is illustrated (in phantom) as a pivotable latch or arm but other retainers such as retractable pins, straps, bands, flexible fingers, detents, and the like may be used if desired.

Figure 4:
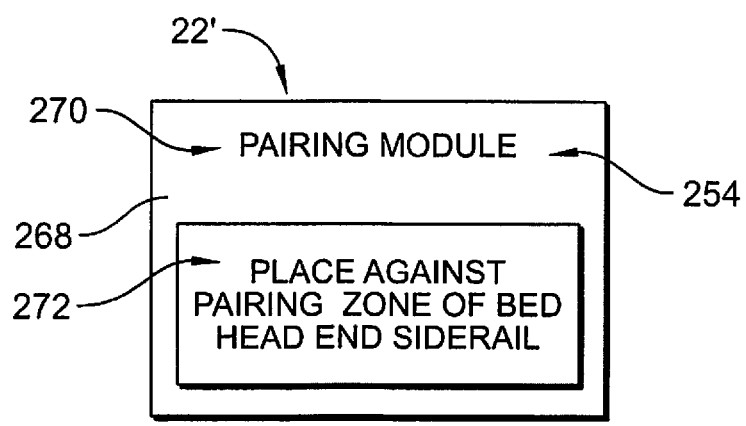
FIG. 4 is a front elevation view of the handheld unit of FIG. 4 showing indicia on a face of the handheld unit with instructions for pairing the handheld unit to the patient bed.

It should be appreciated that cable 28 extending from pairing module 22' is sufficiently long to permit pairing module 22' to be moved from mounting bracket 250 into pairing zone 100 when bed 20 is situated in the patient room at its normal location. For example, suitable lengths for cables 28 are roughly about 3 feet (about 1 meter) to about 7 feet (about 2 meters) but longer cables 28 can be used if desired. As shown in FIG. 4, a front wall 268 of housing 254 of pairing module 22' has first text 270 which states "PAIRING MODULE" and second text 272 which states "PLACE AGAINST PAIRING ZONE OF BED HEAD END SIDERAIL." Thus, text 270 informs caregivers of the identity of the pairing module 22' and text 272 informs caregivers how to use pairing module 22' to establish wireless communications 102, 104 between the pairing module 22' and bed 20.

Text 272 is included as indicia on a label that is adhered to front wall 268 of housing 254 in some embodiments. In other embodiments, text 272 includes indicia printed directly onto front wall 268 of housing 254. Similarly, text 270 may be included as indicia printed on a corresponding label or printed directly on front wall 268 of housing 254. In still other embodiments, text 270, 272 may be embossed, debossed, stamped, or otherwise formed integrally with front wall 268 of housing 254. In a similar manner, pillow speaker 22 may include text 272 to instruct caregivers how to use pillow speaker 22 to establish wireless communications 102, 104 between pillow speaker 22 and bed 20. Text 272 may be provided on the back wall of housing 32 of pillow speaker 22, for example.

Figure 5:
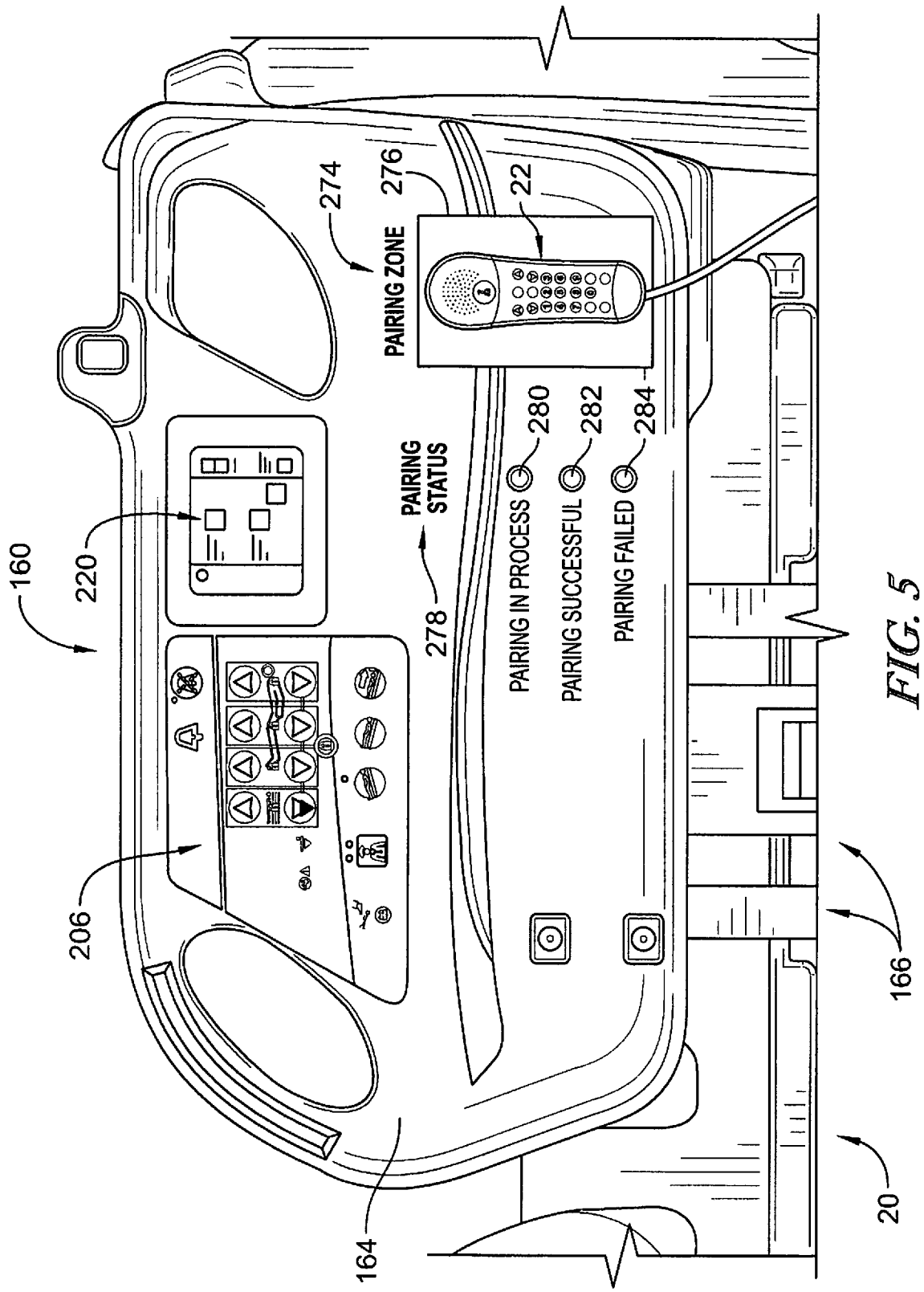
FIG. 5 is a side elevation view of a head end siderail of the patient bed showing a pairing zone designated at a head end region of the siderail and showing pairing status indicators adjacent the pairing zone.

Referring now to FIG. 5, one of siderails 160 is shown and has text or indicia 274 on barrier panel 164 that states "PAIRING ZONE" and a rectangular box 276 is provided beneath text 274 to indicate where pillow speaker 22 or pairing module 22' should be placed with respect to the siderail 160 to allow for wireless communications 102, 104 to be established between bed 20 and the pillow speaker 22 or pairing module 22' as the case may be. Basically, pairing zone 100 is provided in the space outboard of box 276. In the description that follows with regard to FIGS. 5-8, pillow speaker 22 is shown in the pairing zone 100 adjacent to siderail 160 in the vicinity of box 276 but the description is equally applicable to pairing module 22' being situated in the pairing zone 100 the vicinity of box 276.

Panel 164 further includes text or indicia 278 which states "PAIRING STATUS" and first, second, and third indicator lights 280, 282, 284 thereunder. Lights 280, 282, 284 are light emitting diodes (LED's), for example. Adjacent to indicator light 280 is the text "PAIRING IN PROCESS" to indicate by illumination of light 280 that NFC reader 222 has detected the NFC transponder 224 and that the process of pairing bed 20 with pillow speaker 22 has begun. Adjacent to indicator light 282 is the text "PAIRING SUCCESSFUL" to indicate by illumination of light 282 that BT/BLE pairing between bed 20 and pillow speaker 22 has successfully occurred. Adjacent to indicator light 284 is the text "PAIRING FAILED" to indicate by illumination of light 284 that BT/BLE pairing was not successful for some reason. It is contemplated that only one of indicators lights 280, 282, 284 is illuminated at a time such that when light 282 or light 284 becomes illuminated or turned on, light 280 is turned off. Of course, if pillow speaker 22 is not within pairing zone 100 in the vicinity of box 276, the all three of indicator lights 280, 282, 284 are turned off.

In a variant embodiment, only a single pairing status indicator is provided and is illuminated yellow to indicate pairing in process, then is illuminated either green to indicated successful pairing or red to indicate failed pairing. In such an embodiment, appropriate text is provided adjacent to the indicator to explain the meaning of the illumination colors. In still a further variant, two pairing status indicators are provided in which the first indicator is illuminated to indicate pairing in process and then the second indicator is illuminated either green to indicate successful pairing or red to indicate failed pairing.

Figure 6:
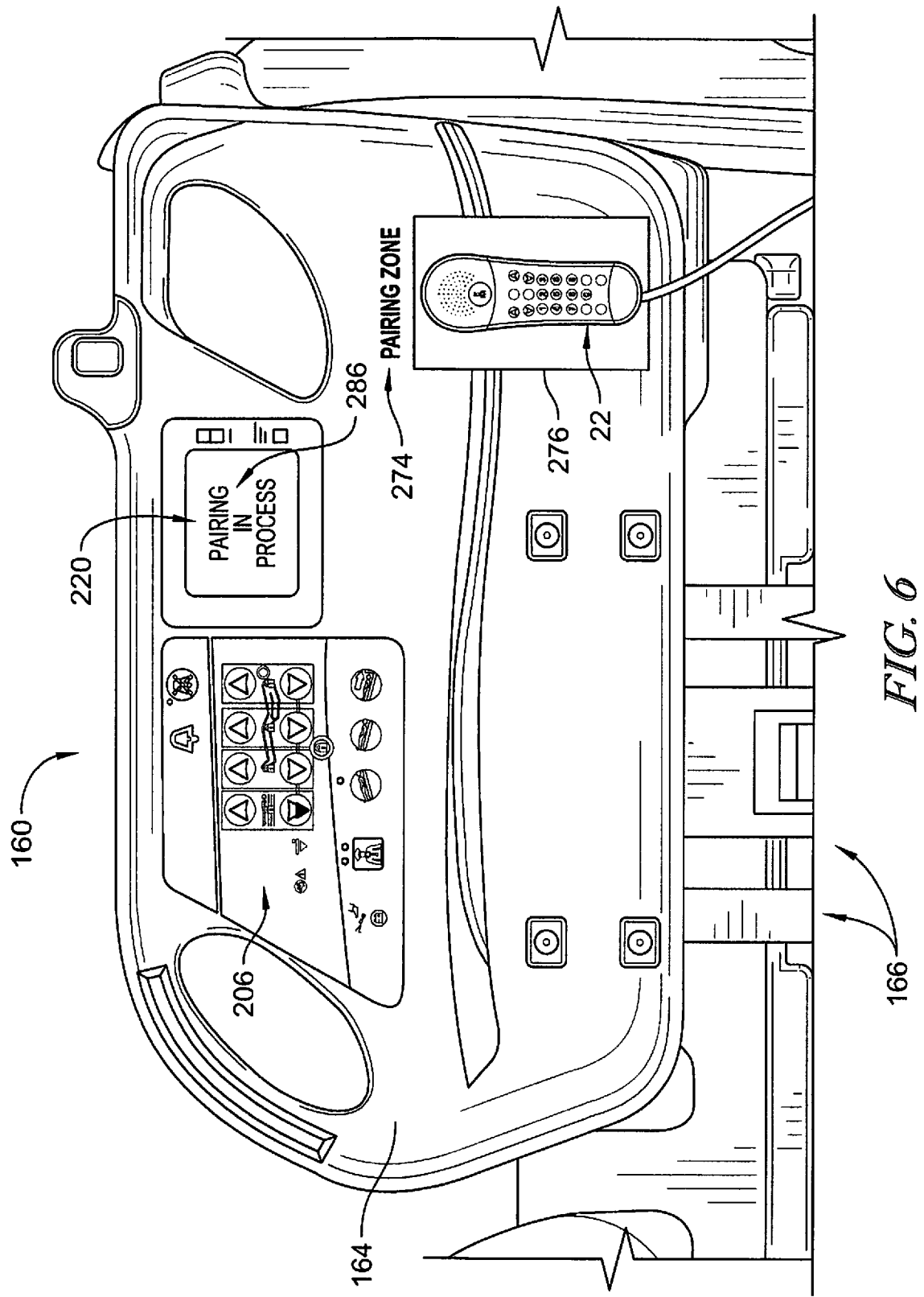
FIG. 6 is a side elevation view of the head end siderail, similar to FIG. 5 but omitting the pairing status indicators, showing the pillow speaker placed in the pairing zone adjacent the siderail and showing a graphical user interface (GUI) displaying a "PAIRING IN PROCESS" message to indicate the status of the pairing operation.
Figure 7:
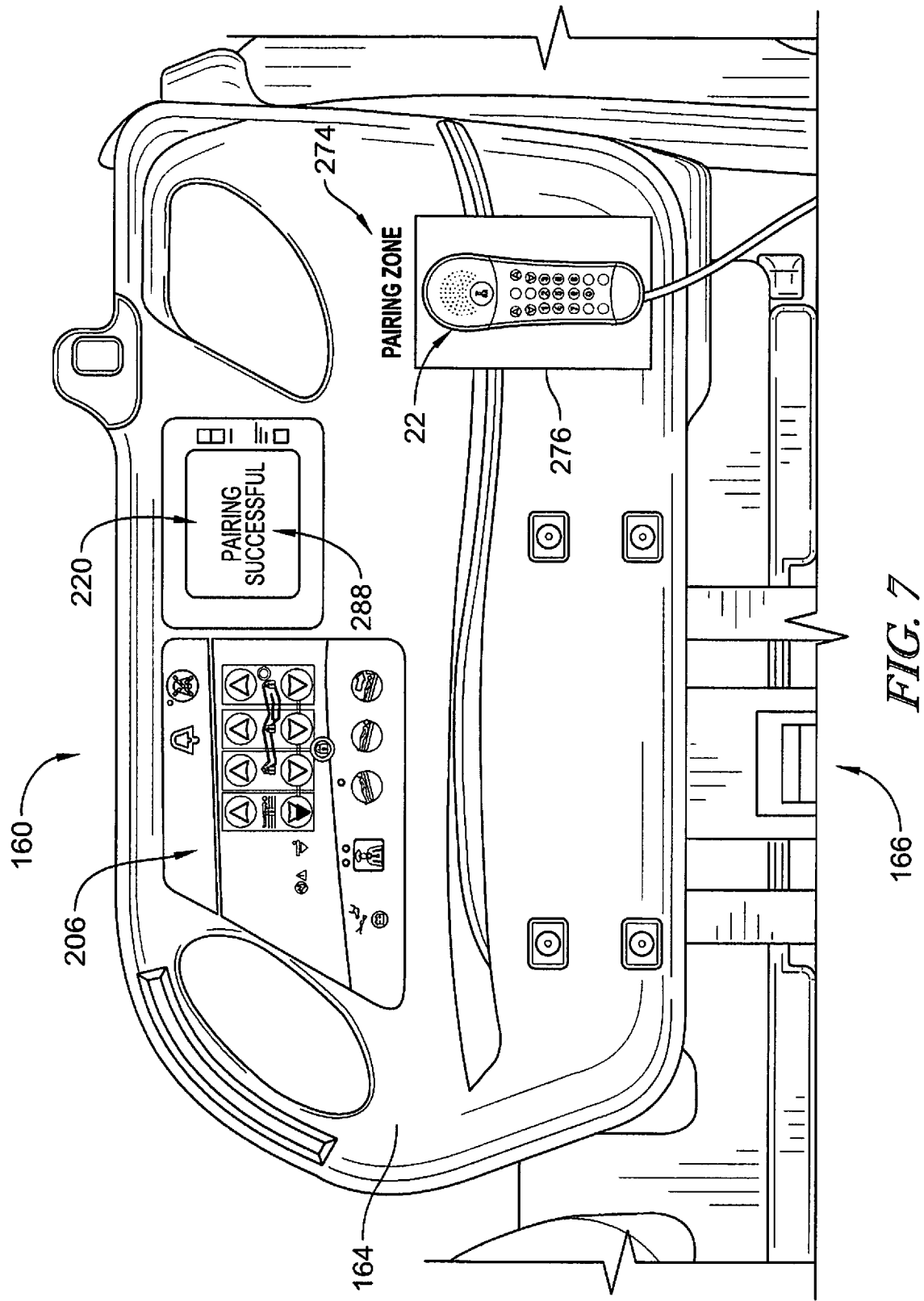
FIG. 7 is a side elevation view of the head end siderail, similar to FIG. 6, showing the GUI displaying a "PAIRING SUCCESSFUL" message to indicate that the pillow speaker has been successfully wirelessly paired with the patient bed.
Figure 8:
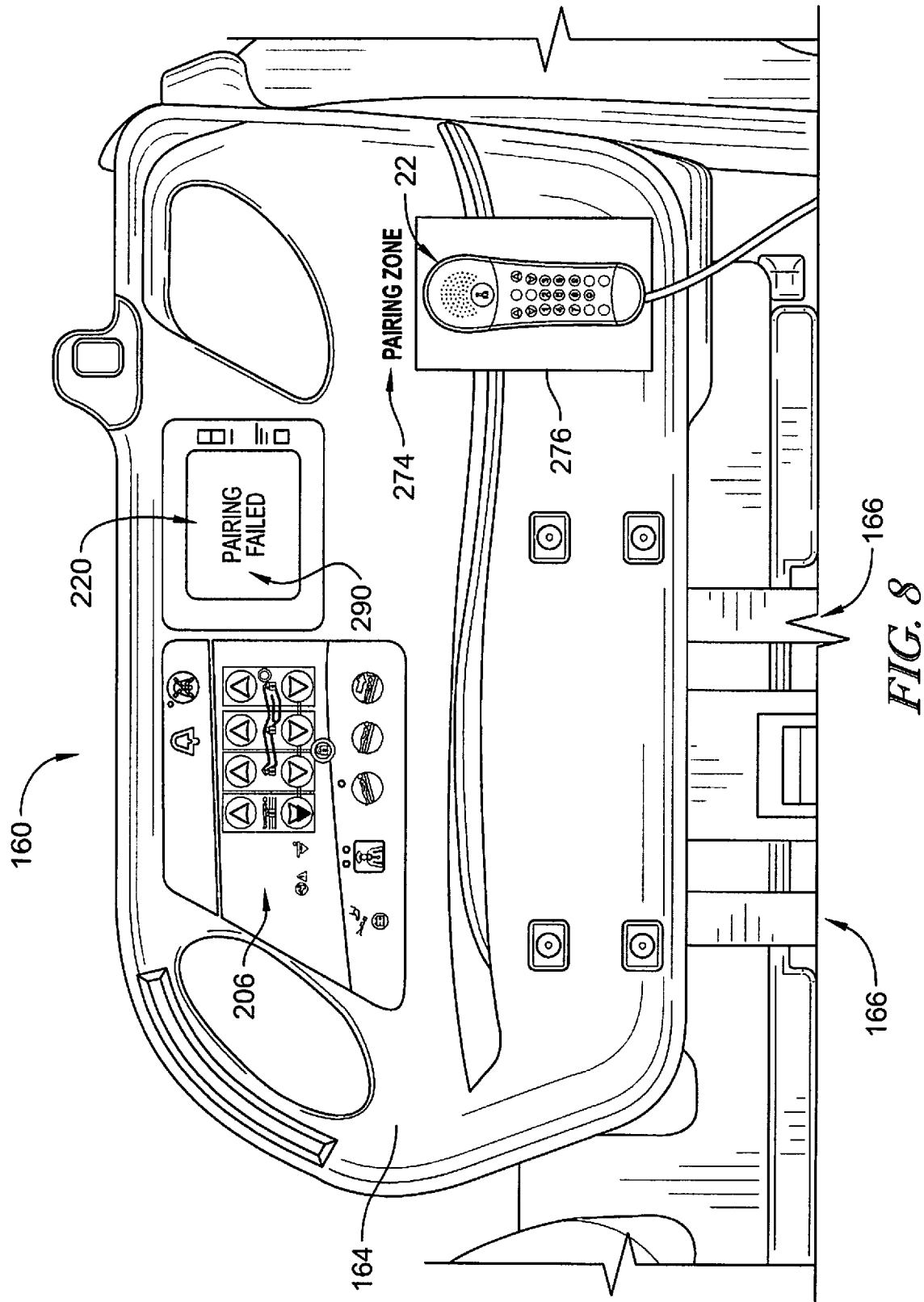
FIG. 8 is a side elevation view of the head end siderail, similar to FIGS. 6 and 7, showing the GUI displaying a "PAIRING FAILED" message to indicate that the pillow speaker has not been successfully wirelessly paired with the patient bed.

Referring now to FIGS. 6-8, an alternative embodiment of bed 20 is shown in which indicator lights 280, 282, 284 are omitted and the pairing status between pillow speaker 22 and bed 20 is indicated by messages on GUI 220. For example, in FIG. 6, a text message 286 including the text "PAIRING IN PROCESS" appears on GUI 220 to indicate that NFC reader 222 has detected the NFC transponder 224 and that the process of pairing bed 20 with pillow speaker 22 has begun. In FIG. 7, a text message 288 including the text "PAIRING SUCCESSFUL" appears on GUI 220 to indicate that BT/BLE pairing between bed 20 and pillow speaker 22 has successfully occurred. In FIG. 8, a text message 290 including the text "PAIRING FAILED" appears on GUI 220 to indicate that BT/BLE pairing was not successful for some reason. It is contemplated that only one of messages 286, 288, 290 appears on GUI 220 at a time such that when message 288 or message 290 appears on GUI 220, message 286 disappears from GUI 220. Of course, if pillow speaker 22 is not within pairing zone 100 in the vicinity of box 276, none of messages 286, 288, 290 appear on GUI 220.

In some embodiments, messages 286, 288, 290 appear in pop-up windows that overlie a portion of whatever screen was previously being shown on GUI 220. After a predetermined period of time such as about 5 seconds to about 30 seconds, messages 288, 290 automatically disappear from GUI 220 in some embodiments. In other embodiments, a close button or icon appears next to messages 288, 290 for selection by a caregiver to close the particular message 288, 290 from appearing on GUI 220 and to return the caregiver back to the previous screen being viewed on GUI 220.

According to the present disclosure, in some embodiments of system 10, the NFC wireless communications link 102 between bed 10 and either pillow speaker 22 or pairing module 22', as the case may be, is omitted. Accordingly, the NFC reader 222 and associated antenna 226 along with the NFC transponder 224 are omitted. In such embodiments, the BT/BLE wireless communications link 104 is established by pairing bed 20 with pillow speaker 22 or pairing module 22' in response to selections made by a caregiver or other user on GUI 220. In particular, a menu of devices that have BT/BLE communication capability and that are within the reception range of BT/BLE communication range of bed 20 are listed in a menu on GUI 220. The user then selects the desired pillow speaker 22 or paring module 22' with which bed 20 is to pair from the menu such as by touching the desired item on the GUI 220 and then pressing a button or icon to confirm the selection. A BT/BLE pairing disconnect button is also provided on GUI 220 for selection in some embodiments, including in embodiments having NFC reader 222, antenna 226, and transponder 224, so that the BT/BLE pairing between bed 20 and pillow speaker 22 or pairing module 22' can be terminated. The pairing is also terminated if bed 20 and the paired device 22, 22' are no longer within reception range of each other for a threshold period of time, such as a about 30 seconds to about 2 minutes just to give an arbitrary time threshold range.

Additional details of such BT/BLE pairing and disconnection via selections on a GUI of a bed is shown for example in U.S. Patent Application Publication No. 2018/0161225 A1 which is already incorporated by reference herein (see particularly FIGS. 268-285 and the related descriptions thereof). See also, U.S. Patent Application Publication No. 2016/0307429 A1 which is hereby incorporated by reference herein to the extent not inconsistent with the present disclosure which shall control as to any inconsistencies (see particularly FIGS. 6 and 7 and the related descriptions thereof). For manual pairing using GUI 220, after BT/BLE module 242 detects a broadcast from BT/BLE module 234 of pillow speaker 22 or pairing module 22', as the case may be, a pairing ID corresponding to the pillow speaker 22 or module 22' is included on the list of devices that are within BT/BLE reception range of bed 20. The pairing ID appearing on GUI 220 is also shown on the outside of pillow speaker 22 or module 22' such as being printed on an outer surface of housing 32 or housing 254 or included on a label that is adhered to an outer surface of housing 32 or housing 254, for example. Thus, the user views the pairing ID on pillow speaker 22 or module 22' and then selects the corresponding pairing ID on GUI 220 to initiate the pairing between bed 20 and the selected pillow speaker 22 or module 22'.

After bed 20 is paired with pillow speaker 22 or pairing module 22', bed status data, including alert data, is sent via the BT/BLE wireless communications link 104 (or link 104') from bed 20 to pillow speaker 22 or pairing module 22' as the case may be. More particularly, the bed status data is sent over link 104 (or link 104') by BT/BLE module 242 using antenna 244 or using antenna 246 (with regard to link 104') for the transmission that is then received by antenna 236 of BT/BLE module 234 of pillow speaker 22 or pairing module 22'. Pillow speaker 22 or pairing module 22', as the case may be, then transmits the bed status data via cable 28 from circuitry 228 to wall module 30 which, in turn, transmits the bed status data to nurse call system 40. Wall module 30 also transmits a location ID along with the bed status data to nurse call system 40. The location ID stored in memory of wall module 30 correlates to the patient room at which bed 20 is located. Nurse call server 86 of nurse call system 40 stores the bed status data, including the location ID, and, in some embodiments, transmits some or all of the bed status data to other portions of system 10 such as to EMR server 94, RTLS 39, and so forth. The location ID stored in memory of wall module 30 may include for example, a wall module ID, a MAC address of an integrated circuit chip (e.g., microprocessor or microcontroller) of wall module 30, or some other randomly assigned ID that correlates to the room location of wall module 30.

Bed status data, including alert data, is also sent from each of beds 20 via the corresponding WiFi communications link 106 (or link 106') to one or more of WAP's 24 which, in turn, transmits the bed status data to bed data server 92. Bed data server 92 may be a cloud-based server in some embodiments that is remote from the healthcare facility in which beds 20 are located. In some embodiments, the room location corresponding to the location ID transmitted from wall module 30 to nurse call system 40 is, in turn, transmitted to the corresponding bed 20 using the WiFi communication link 106 (or link 106'). Bed 20 then stores the room location in memory 214 and displays the room location on GUI 220 in some embodiments. The present disclosure also contemplates that, in some embodiments, wall module 30 is able to transmit the location ID to pillow speaker 22 or pairing module 22' via cable 28 and then the pillow speaker 22 or pairing module 22', as the case may be, then transmits the location ID to bed 20 via BT/BLE communications link 104 or BT/BLE communications link 104' as the case may be.

The present disclosure further contemplates that the bed status data sent from bed 20 via wireless communication links 104, 104', 106, 106' includes any and all bed status data available on bed 20. Such data includes, but is not limited to, nurse calls, nurse call audio (e.g., bidirectional audio between a nurse call station, such as the master nurse station 78, staff station 80, or graphical audio station 64, and bed 20), bed exit alarms, bed type, bed ID (e.g., bed serial number), bed exit system armed/disarmed status, brake status (e.g., braked or unbraked), siderail position status (e.g., raised or lowered), motor lockout status (e.g., whether any of motors 190, 192, 194, 196, 200 are locked out from use), emergency cardiopulmonary (CPR) switch status (e.g., whether an emergency CPR release to rapidly lower head section 180 has been pulled), battery status (e.g., charge state of battery), HOB alarm status, status of alert lights 126, 128, 130, incontinence detection alerts (e.g., if an incontinence detection system is included on bed 20), data sensed by HR/RR sensor 223, bed inputs make (e.g., an indication of which features are supported by the bed 20), status of inflating and deflating at least one bladder of mattress 144 (e.g., data pertaining to the use of pneumatic system 198 to inflate or deflate patient support bladders or turning bladders), and patient weight (e.g., measured by scale system 170). The terms "alerts" and "alarms" are used interchangeably herein.

In some embodiments, only a portion of the available bed status data is sent over wireless communication links 104, 104', 106, 106'. For example, in some embodiments, alert data (e.g., nurse calls, bed exit alerts, siderail down alerts, brake release alerts, HOB alerts, etc.) are transmitted from bed 20 via BT/BLE wireless communication link 104 (or link 104') and other bed status data not pertaining to the various bed alerts is transmitted from bed 20 via WiFi communication link 106 (or link 106'). Which bed status data is transmitted over which communication links 104, 106 (or links 104', 106') is at the discretion of the programmer of the software of bed 20. Thus, the same bed status data may be transmitted over both links 104, 106 (or links 104', 106'), or the bed status data transmitted over links 104, 106 (or links 104', 106') may be mutually exclusive of each other, or there may be overlap between some but not all of the bed status data that are transmitted over links 104, 106 (or links 104', 106').

It is also possible for some bed status data to be transmitted over only one of links 104, 106 under certain conditions and to be transmitted over only the other of links 104, 106 under other conditions. For example, if the HOB angle monitoring feature is enabled on bed 20, then HOB angle data may be sent over link 104 (or link 104') and not over link 106 (or link 106'). On the other hand, if the HOB angle monitoring feature is disabled on bed 20, then HOB angle data may be sent over link 106 (or link 106') and not over link 104 (or link 104'). The same scenario can be implemented in connection with monitoring of some or all of siderail position status, bed height status, and caster brake status, for example. In variant embodiments, if the HOB angle monitoring feature is enabled on bed 20, then HOB angle data may be sent over both of links 104, 106 (or both of links 104', 106) but then only over link 106 (or 106') if the HOB angle monitoring feature is disabled on bed 20. This variant scenario can also be implemented in connection with some or all of siderail position status, bed height status, and caster brake status, if desired.

When terms of degree such as "substantially" and "about" are used herein in connection with a numerical value or a qualitative term susceptible to a numerical definition (e.g., vertical, horizontal, aligned), it is contemplated that an amount that is plus or minus 10 percent, and possibly up to plus or minus 20 percent, of the numerical value is covered by such language. For example, "vertical" may be defined as 90 degrees from horizontal and so "substantially vertical" according to the present disclosure means 90 degrees plus or minus 9 degrees, and possibly up to plus or minus 18 degrees. The same tolerance range for "substantially horizontal" is also contemplated. Otherwise, a suitable definition for "substantially" is largely, but not necessarily wholly, the term specified.

Although certain illustrative embodiments have been described in detail above, variations and modifications exist within the scope and spirit of this disclosure as described and as defined in the following claims.

The invention claimed is:

1. A system of patient bed communication and bed-to-room association in a healthcare facility having a network with at least one wireless access point (WAP) and a nurse call system, the system comprising
a patient bed including a frame and circuitry carried by the frame, the circuitry including a first portion configured for wireless communication according to a first wireless communication technology, a second portion configured for wireless communication according to a second wireless communication technology, and a third portion configured for wireless communication according to a third wireless communication technology, and
a handheld unit having a wired connection to the nurse call system, the handheld unit having wireless bed interface circuitry in communication with the patient bed according to the first and second wireless communication technologies but not the third wireless communication technology,
wherein the first wireless communication technology is used to perform a pairing operation between the patient bed and the handheld unit in response to the handheld unit being manually placed within a pairing distance of four centimeters or less of a pairing zone of the patient bed,
wherein the second wireless communication technology is used to send bed identification data (ID) to the handheld unit after the pairing operation has been completed and with the handheld unit being at a communication distance greater than the pairing distance from the pairing zone, the handheld unit being configured to transmit the bed ID to the nurse call system to establish a bed-to-room association between the patient bed and a room in which the patient bed is located,
wherein the third wireless communication technology is used to send bed status data and the bed ID to the WAP of the network,
wherein the circuitry of the patient bed includes a processor and a memory, the memory storing instructions that are executed by the processor to control or monitor features of the patient bed,
wherein the features of the patient bed include one or more of the following: moving a first portion of the frame relative to a second portion of the frame, inflating or deflating a bladder of a mattress supported by the frame, detecting a position of a siderail coupled to the frame, detecting a caster brake status of one or more casters of the frame, detecting an angle of a head section of the frame relative to horizontal or relative to another portion of the frame, detecting a bed exit system of the patient bed being armed, detecting a patient weight using a weigh scale of the frame, or detecting an upper frame portion of the frame being in a lowest position of the upper frame relative to a base frame portion of the frame.

2. The system of claim 1, wherein the first wireless communication technology comprises near field communication (NFC) technology.

3. A system of patient bed communication and bed-to-room association in a healthcare facility having a network with at least one wireless access point (WAP) and a nurse call system, the system comprising
a patient bed including a frame and circuitry carried by the frame, the circuitry including a first portion configured for wireless communication according to a first wireless communication technology, a second portion configured for wireless communication according to a second wireless communication technology, and a third portion configured for wireless communication according to a third wireless communication technology, and
a handheld unit having a wired connection to the nurse call system, the handheld unit having wireless bed interface circuitry in communication with the patient bed according to the first and second wireless communication technologies but not the third wireless communication technology,
wherein the first wireless communication technology is used to perform a pairing operation between the patient bed and the handheld unit in response to the handheld unit being manually placed within a pairing distance of four centimeters or less of a pairing zone of the patient bed,
wherein the second wireless communication technology is used to send bed identification data (ID) to the handheld unit after the pairing operation has been completed and with the handheld unit being at a communication distance greater than the pairing distance from the pairing zone, the handheld unit being configured to transmit the bed ID to the nurse call system to establish a bed-to-room association between the patient bed and a room in which the patient bed is located,
wherein the third wireless communication technology is used to send bed status data and the bed ID to the WAP of the network,
wherein the first wireless communication technology comprises near field communication (NFC) technology,
wherein the frame of the patient bed includes a siderail that is movable between a raised position to block a patient from egressing from the patient bed and a lowered position to permit the patient to egress from the patient bed, and wherein the pairing zone is provided on the siderail.

4. The system of claim 3, further comprising indicia on the siderail to visually indicate where the pairing zone is located on the siderail.

5. The system of claim 2, wherein the second wireless communication technology comprises Bluetooth technology.

6. A system of patient bed communication and bed-to-room association in a healthcare facility having a network with at least one wireless access point (WAP) and a nurse call system, the system comprising
- a patient bed including a frame and circuitry carried by the frame, the circuitry including a first portion configured for wireless communication according to a first wireless communication technology, a second portion configured for wireless communication according to a second wireless communication technology, and a third portion configured for wireless communication according to a third wireless communication technology, and
- a handheld unit having a wired connection to the nurse call system, the handheld unit having wireless bed interface circuitry in communication with the patient bed according to the first and second wireless communication technologies but not the third wireless communication technology,
- wherein the first wireless communication technology is used to perform a pairing operation between the patient bed and the handheld unit in response to the handheld unit being manually placed within a pairing distance of four centimeters or less of a pairing zone of the patient bed,
- wherein the second wireless communication technology is used to send bed identification data (ID) to the handheld unit after the pairing operation has been completed and with the handheld unit being at a communication distance greater than the pairing distance from the pairing zone, the handheld unit being configured to transmit the bed ID to the nurse call system to establish a bed-to-room association between the patient bed and a room in which the patient bed is located,
- wherein the third wireless communication technology is used to send bed status data and the bed ID to the WAP of the network,
- wherein the first wireless communication technology comprises near field communication (NFC) technology,
- wherein the second wireless communication technology comprises Bluetooth technology,
- wherein the Bluetooth technology comprises Bluetooth Low Energy (BLE) technology.

7. A system of patient bed communication and bed-to-room association in a healthcare facility having a network with at least one wireless access point (WAP) and a nurse call system, the system comprising
- a patient bed including a frame and circuitry carried by the frame, the circuitry including a first portion configured for wireless communication according to a first wireless communication technology, a second portion configured for wireless communication according to a second wireless communication technology, and a third portion configured for wireless communication according to a third wireless communication technology, and
- a handheld unit having a wired connection to the nurse call system, the handheld unit having wireless bed interface circuitry in communication with the patient bed according to the first and second wireless communication technologies but not the third wireless communication technology,
- wherein the first wireless communication technology is used to perform a pairing operation between the patient bed and the handheld unit in response to the handheld unit being manually placed within a pairing distance of four centimeters or less of a pairing zone of the patient bed,
- wherein the second wireless communication technology is used to send bed identification data (ID) to the handheld unit after the pairing operation has been completed and with the handheld unit being at a communication distance greater than the pairing distance from the pairing zone, the handheld unit being configured to transmit the bed ID to the nurse call system to establish a bed-to-room association between the patient bed and a room in which the patient bed is located,
- wherein the third wireless communication technology is used to send bed status data and the bed ID to the WAP of the network,
- wherein the first wireless communication technology comprises near field communication (NFC) technology,
- wherein the second wireless communication technology comprises Bluetooth technology,
- wherein the Bluetooth technology is used to send audio signals between the patient bed and the handheld unit.

8. A system of patient bed communication and bed-to-room association in a healthcare facility having a network with at least one wireless access point (WAP) and a nurse call system, the system comprising
- a patient bed including a frame and circuitry carried by the frame, the circuitry including a first portion configured for wireless communication according to a first wireless communication technology, a second portion configured for wireless communication according to a second wireless communication technology, and a third portion configured for wireless communication according to a third wireless communication technology, and
- a handheld unit having a wired connection to the nurse call system, the handheld unit having wireless bed interface circuitry in communication with the patient bed according to the first and second wireless communication technologies but not the third wireless communication technology,
- wherein the first wireless communication technology is used to perform a pairing operation between the patient bed and the handheld unit in response to the handheld unit being manually placed within a pairing distance of four centimeters or less of a pairing zone of the patient bed,
- wherein the second wireless communication technology is used to send bed identification data (ID) to the handheld unit after the pairing operation has been completed and with the handheld unit being at a communication distance greater than the pairing distance from the pairing zone, the handheld unit being configured to transmit the bed ID to the nurse call system to establish a bed-to-room association between the patient bed and a room in which the patient bed is located,
- wherein the third wireless communication technology is used to send bed status data and the bed ID to the WAP of the network, wherein the first wireless communication technology comprises near field communication (NFC) technology, wherein the second wireless communication technology comprises Bluetooth technology, wherein the third wireless communication technology comprises WiFi technology according to an 802.11 communication protocol.

9. The system of claim 1, wherein the wired connection to the nurse call system comprises a cable having a first connector that couples to a second connector of a wall module of the nurse call system.

10. A system of patient bed communication and bed-to-room association in a healthcare facility having a network with at least one wireless access point (WAP) and a nurse call system, the system comprising a patient bed including a frame and circuitry carried by the frame, the circuitry including a first portion configured for wireless communication according to a first wireless communication technology, a second portion configured for wireless communication according to a second wireless communication technology, and a third portion configured for wireless communication according to a third wireless communication technology, and a handheld unit having a wired connection to the nurse call system, the handheld unit having wireless bed interface circuitry in communication with the patient bed according to the first and second wireless communication technologies but not the third wireless communication technology, wherein the first wireless communication technology is used to perform a pairing operation between the patient bed and the handheld unit in response to the handheld unit being manually placed within a pairing distance of four centimeters or less of a pairing zone of the patient bed, wherein the second wireless communication technology is used to send bed identification data (ID) to the handheld unit after the pairing operation has been completed and with the handheld unit being at a communication distance greater than the pairing distance from the pairing zone, the handheld unit being configured to transmit the bed ID to the nurse call system to establish a bed-to-room association between the patient bed and a room in which the patient bed is located, wherein the third wireless communication technology is used to send bed status data and the bed ID to the WAP of the network, wherein the wired connection to the nurse call system comprises a cable having a first connector that couples to a second connector of a wall module of the nurse call system, wherein the wall module sends a location ID along with the bed ID for receipt by a nurse call server of the nurse call system, the location ID corresponding to the room in which the patient bed is located and being used to establish the bed-to-room association.

11. The system of claim 1, wherein the handheld unit comprises a pillow speaker that includes user inputs for (i) sending a nurse call signal to the nurse call system, (ii) controlling room lighting, and (iii) controlling at least one room entertainment device.

12. The system of claim 1, wherein the bed status data sent to the WAP of the network includes information regarding the features of the patient bed.

13. The system of claim 1, wherein the instructions stored in memory are also executed by the processor to determine alert conditions associated with the patient bed.

14. A system of patient bed communication and bed-to-room association in a healthcare facility having a network with at least one wireless access point (WAP) and a nurse call system, the system comprising a patient bed including a frame and circuitry carried by the frame, the circuitry including a first portion configured for wireless communication according to a first wireless communication technology, a second portion configured for wireless communication according to a second wireless communication technology, and a third portion configured for wireless communication according to a third wireless communication technology, and a handheld unit having a wired connection to the nurse call system, the handheld unit having wireless bed interface circuitry in communication with the patient bed according to the first and second wireless communication technologies but not the third wireless communication technology, wherein the first wireless communication technology is used to perform a pairing operation between the patient bed and the handheld unit in response to the handheld unit being manually placed within a pairing distance of four centimeters or less of a pairing zone of the patient bed, wherein the second wireless communication technology is used to send bed identification data (ID) to the handheld unit after the pairing operation has been completed and with the handheld unit being at a communication distance greater than the pairing distance from the pairing zone, the handheld unit being configured to transmit the bed ID to the nurse call system to establish a bed-to-room association between the patient bed and a room in which the patient bed is located, wherein the third wireless communication technology is used to send bed status data and the bed ID to the WAP of the network, wherein the circuitry of the patient bed includes a processor and a memory, the memory storing instructions that are executed by the processor to control or monitor features of the patient bed, wherein the instructions stored in memory are also executed by the processor to determine alert conditions associated with the patient bed, wherein the alert conditions comprise one or more of the following: a head section of the frame being lowered below a threshold angle relative to horizontal or relative to another portion of the frame, a siderail coupled to the frame being lowered, a patient exiting the patient bed, a patient moving to an unwanted position on the patient bed, an inability of a bladder of a mattress supported by the frame to be inflated to a target pressure, one or more casters of the frame becoming unbraked, an upper frame portion of the frame being moved out of a lowest position of the upper frame relative to a base frame portion of the frame, or a patient becoming incontinent on the patient bed.

15. The system of claim 14, wherein the bed status data sent to the WAP of the network includes information regarding the alert conditions.

16. The system of claim 1, further comprising a wall mount to which the handheld unit is detachably coupleable and wherein the wired connection comprises a cable of sufficient length to permit the handheld unit to be moved to the pairing zone of the patient bed after the handheld unit has been detached from the wall mount.

17. A system of patient bed communication and bed-to-room association in a healthcare facility having a network with at least one wireless access point (WAP) and a nurse call system, the system comprising
   a patient bed including a frame and circuitry carried by the frame, the circuitry including a first portion configured for wireless communication according to a first wireless communication technology, a second portion configured for wireless communication according to a second wireless communication technology, and a third portion configured for wireless communication according to a third wireless communication technology,
   a handheld unit having a wired connection to the nurse call system, the handheld unit having wireless bed interface circuitry in communication with the patient bed according to the first and second wireless communication technologies but not the third wireless communication technology, and
   a wall mount to which the handheld unit is detachably coupleable and wherein the wired connection comprises a cable of sufficient length to permit the handheld unit to be moved to the pairing zone of the patient bed after the handheld unit has been detached from the wall mount,
   wherein the first wireless communication technology is used to perform a pairing operation between the patient bed and the handheld unit in response to the handheld unit being manually placed within a pairing distance of four centimeters or less of a pairing zone of the patient bed,
   wherein the second wireless communication technology is used to send bed identification data (ID) to the handheld unit after the pairing operation has been completed and with the handheld unit being at a communication distance greater than the pairing distance from the pairing zone, the handheld unit being configured to transmit the bed ID to the nurse call system to establish a bed-to-room association between the patient bed and a room in which the patient bed is located,
   wherein the third wireless communication technology is used to send bed status data and the bed ID to the WAP of the network,
   wherein the handheld unit is devoid of any manual user inputs.

18. A system of patient bed communication and bed-to-room association in a healthcare facility having a network with at least one wireless access point (WAP) and a nurse call system, the system comprising
   a patient bed including a frame and circuitry carried by the frame, the circuitry including a first portion configured for wireless communication according to a first wireless communication technology, a second portion configured for wireless communication according to a second wireless communication technology, and a third portion configured for wireless communication according to a third wireless communication technology,
   a handheld unit having a wired connection to the nurse call system, the handheld unit having wireless bed interface circuitry in communication with the patient bed according to the first and second wireless communication technologies but not the third wireless communication technology, and
   a wall mount to which the handheld unit is detachably coupleable and wherein the wired connection comprises a cable of sufficient length to permit the handheld unit to be moved to the pairing zone of the patient bed after the handheld unit has been detached from the wall mount,
   wherein the first wireless communication technology is used to perform a pairing operation between the patient bed and the handheld unit in response to the handheld unit being manually placed within a pairing distance of four centimeters or less of a pairing zone of the patient bed,
   wherein the second wireless communication technology is used to send bed identification data (ID) to the handheld unit after the pairing operation has been completed and with the handheld unit being at a communication distance greater than the pairing distance from the pairing zone, the handheld unit being configured to transmit the bed ID to the nurse call system to establish a bed-to-room association between the patient bed and a room in which the patient bed is located,
   wherein the third wireless communication technology is used to send bed status data and the bed ID to the WAP of the network,
   wherein the handheld unit includes indicia providing instructions regarding the pairing operation.

19. The system of claim 3, wherein the patient bed includes at least one indicator or at least one graphical user interface (GUI) operable to display a status of the pairing operation.

20. The system of claim 14, wherein the patient bed includes at least one indicator or at least one graphical user interface (GUI) operable to display a status of the pairing operation.

* * * * *